(12) United States Patent
Nakajo et al.

(10) Patent No.: US 6,610,717 B2
(45) Date of Patent: Aug. 26, 2003

(54) DIHYDROPYRIDINE DERIVATIVES

(75) Inventors: Akira Nakajo, Kanagawa (JP);
Munetaka Tokumasu, Kanagawa (JP);
Morikazu Kito, Kanagawa (JP); Akira Takahara, Kanagawa (JP); Yukitsugu Ono, Kanagawa (JP); Tomoko Takeda, Kanagawa (JP); Yuki Kajigaya, Kanagawa (JP); Hajime Koganei, Kanagawa (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 10/023,813

(22) Filed: Dec. 21, 2001

(65) Prior Publication Data

US 2002/0193605 A1 Dec. 19, 2002

Related U.S. Application Data

(63) Continuation of application No. PCT/JP00/04106, filed on Jun. 22, 2000.

(30) Foreign Application Priority Data

Jun. 23, 1999 (JP) .......................................... 11-177492

(51) Int. Cl.[7] ........................ A61K 31/44; A61K 31/41; C07D 401/00; C07D 213/44
(52) U.S. Cl. ...................... 514/365; 514/336; 514/340; 546/256; 546/262
(58) Field of Search ............................... 514/355, 336, 514/340; 546/256, 262

(56) References Cited

U.S. PATENT DOCUMENTS

| 4,540,684 A | | 9/1985 | Stoltefuss et al. | |
| 4,616,002 A | | 10/1986 | Kamber et al. | |
| 5,051,433 A | * | 9/1991 | Stoltefuss et al. | .......... 514/356 |
| 5,767,129 A | | 6/1998 | Yuen | |

FOREIGN PATENT DOCUMENTS

| DE | 3833893 | * | 4/1990 |
| EP | 0 127 826 A2 | | 12/1984 |
| EP | 0 220 917 A1 | | 5/1987 |
| EP | 0225 175 A2 | | 6/1987 |
| EP | 0273 349 A2 | | 7/1988 |
| EP | 0 488 345 A1 | | 6/1992 |
| EP | 0 985 667 A1 | | 3/2000 |
| EP | 1 043 314 A1 | | 10/2000 |
| JP | 60-233058 | | 11/1985 |
| JP | 03 223253 A | | 10/1991 |
| JP | 8-40904 | | 2/1996 |
| WO | WO 97/00836 A1 | | 2/1987 |
| WO | WO 87 00836 A1 | | 3/1991 |
| WO | WO 93/13128 | | 7/1993 |
| WO | WO 98/49144 | | 11/1998 |
| WO | WO99/32446 | * | 1/1999 |
| WO | WO 99/32446 | | 7/1999 |
| WO | WO 00/24716 | | 5/2000 |

OTHER PUBLICATIONS

Cooper, Kelvin et al: "Enantiodifferentiation of Dihydropyridine PAF Antagonists", Giorganic & Medicinal Chemistry Letters, vol. 5, No. 24, pps. 3085–3090, 1995.

Virginia D. Monje et al., *A New Conus Peptide Ligand for Ca Channel Subtypes*, Neuropharmacology, vol. 32, No. 11, pp. 1141–1149, 1993.

Hisayuki Uneyama et al., *Blockage of N–type $Ca^{2+}$ Current by Cilnidipine (FRC–8653) in Acutely Dissociated Rat Sympathetic Neurones*, British Journal of Pharmacology vol. 122, pp. 37–42, 1997.

Shigeo Fujii et al., *Effect of Cilnidipine, a Novel Dihydropyridine Ca++ –channel Antagonist, on N–type Ca++ Channel in Rat Dorsal Root Ganglion Neurons* The Journal of Pharmacology and Experimental Therapeutics, vol. 280, No. 3, pp. 1184–1191, 1997.

Inglesi, CA 114:163951, 1990.*
Anana, CA 125:328575, 1996.*

* cited by examiner

*Primary Examiner*—D. Margaret Seaman
(74) *Attorney, Agent, or Firm*—Oblon, Spivak, McClelland, Maier & Neustadt, P.C.

(57) ABSTRACT

Dihydropyridine derivatives represented by the following formula:

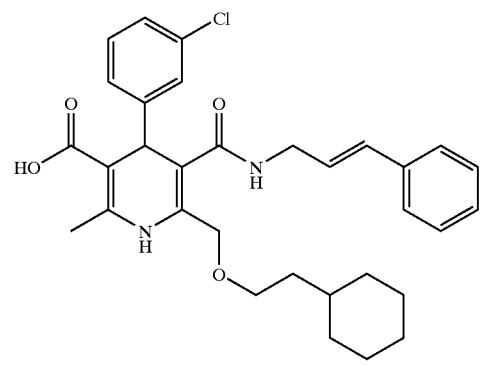

analogs thereof and pharmaceutically acceptable salts thereof have an activity of selectively inhibiting the action of N-type calcium channel, and they are used as therapeutic agents for various diseases relating to N-type calcium channel.

28 Claims, No Drawings

DIHYDROPYRIDINE DERIVATIVES

This application is a Continuation of International application Ser. No. PCT/JP00/04106, filed on Jun. 22, 2000.

BACKGROUND OF THE INVENTION

The present invention relates to new dihydropyridine derivatives and the use of the dihydropyridine derivatives as medicines. The activation of N-type calcium channel is concerned with various diseases, for example, acute stage of ischemic cerebrovascular disorders caused by cerebral infarction or intracerebral bleeding (including subarachnoidal hemorrhage); progressive neurodegenerative diseases such as Alzheimer's disease, AIDS related dementia and Parkinson's disease, dementia due to cerebrovascular disorder and ALS; neuropathy caused by head injury; various pains such as pain caused by spinal injury, diabetes or thromboangiitis obliterans, postoperative pain, migraine and visceral pain; various diseases associated with psychogenic stress such as bronchial asthma, unstable angina and irritable colitis; emotional disorder and withdrawal symptoms after addiction to drugs such as ethanol addiction withdrawal symptoms. The compounds of the present invention can inhibit the activation of the N-type calcium channel and, therefore usable as therapeutic agents for these diseases.

Calcium channels are now classified into subtypes of L, N, P, Q, R and T. Each subtype of calcium channels is organ-specifically distributed. It is known that particularly N-type calcium channel is widely distributed in pars centralis, peripheral nerves and adrenomedullary cells and participates in neuronal cell death, regulation of blood catecholamine level and control of senses such as perception.

It has been confirmed that omega conotoxin GVIA and omega conotoxin MVIIA, which are peptides selectively inhibiting N-type calcium channel, inhibit the release of excitatory neurotransmitters in the sliced brain preparation. It is also confirmed in animal experiments that they inhibit the progress of neuronal necrosis associated with cerebrovascular disorders. It is generally considered that compounds having a N-type calcium channel blocking action are clinically effective in the treatment of acute stage of ischemic cerebrovascular disorders caused by cerebral infarction or intracerebral bleeding (including subarachnoidal hemorrhage); progressive neurodegenerative diseases such as Alzheimer's disease, AIDS related dementia and Parkinson's disease, dementia due to cerebrovascular disorder and ALS; and neuropathy caused by head injury. Further, it is confirmed in animal tests that omega conotoxin MVIIA relieves a pain induced by formaldehyde, hot plate and peripheral neuropathy. Accordingly, omega conotoxin MVIIA is considered to be clinically effective against various pains such as pain caused by spinal injury, diabetes or thromboangiitis obliterans, postoperative pain, migraine and visceral pain. In addition, because omega conotoxin GVIA inhibits the release of catecholamine from cultured sympathetic ganglion cells, catecholamine secretion from canine adrenal medulla and the contraction of the isolated blood vessel by electric stimulation of the perivascular nerve, it is considered that compounds having N-type calcium channel-blocking effects are clinically effective against various diseases related to psychogenic stress such as bronchial asthma, unstable angina and irritable colitis [Neuropharmacol., 32, 1141 (1993)].

Some peptidergic and non-peptidergic compounds which selectively affect N-type calcium channels have been ever disclosed (see, for example, WO 9313128 and WO 9849144). However, none of them was actually used as a medicine. Some of the compounds which affect N-type calcium channels are also effective against various types of calcium channels of other than N-type [British Journal of Pharmacology, 122 (1) 37–42, 1997]. For example, compounds having an antagonistic effect on L-type calcium channels which are very closely related to hypotensive effect, could not be used for diseases for which N-type antagonists will be used (such as cerebral stroke, neuralgia, terminal cancer pain and pain of spinal injury). Under these circumstances, the development of a highly active antagonist selective toward N-type calcium channel has been eagerly demanded.

DISCLOSURE OF THE INVENTION

The object of the present invention is to provide new compounds having a selective antagonistic effect on N-type calcium channels.

Another object of the present invention is to provide antagonists to N-type calcium channels.

Still another object of the present invention is to provide a therapeutic agent for any of acute stage of ischemic cerebrovascular disorders caused by cerebral infarction or intracerebral bleeding, Alzheimer's disease, AIDS related dementia, Parkinson's disease, progressive neurodegenerative diseases, neuropathy caused by head injury, pain caused by thromboangiitis obliterans, postoperative pain, migraine, visceral pain, bronchial asthma, unstable angina, irritable colitis and withdrawal symptoms after addiction to drugs.

A further object of the present invention is to provide a pharmaceutical composition.

After synthesizing various dihydropyridine derivatives and examining the N-type calcium channel inhibiting effect (determined by fluorescent dye method) and L-type calcium channel inhibiting effect of the newly synthesized compounds and well-known dihydropyridine derivatives for the purpose of solving the above-described problems, the inventors have found that specified, new dihydropyridine derivatives have an excellent effect of selectively antagonizing N-type calcium channels. The present invention has been completed on the basis of this finding. Namely, the present invention provides dihydropyridine derivatives of the following general formula (1) and pharmaceutically acceptable salts thereof.

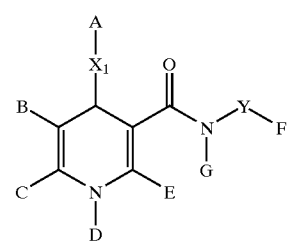

(1)

wherein

A represents a group of the following general formula (2), or 1-naphthyl, 2-naphthyl, thiophene-3-yl, thiophene-2-yl, furan-3-yl, furan-2-yl, pyridine-4-yl, pyridine-3-yl, pyridine-2-yl, indole-2-yl or indole-3-yl group:

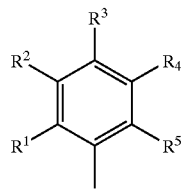
(2)

wherein $R^1$, $R^2$, $R^3$, $R^4$ and $R^5$ may be the same or different from each other and each represent hydrogen atom, a halogen atom, hydroxyl group, carboxyl group, amino group, cyano group, nitro group, a lower alkyl group, a lower alkoxyl group, a lower alkenyl group, a lower alkynyl group, a lower alkylamino group, a lower alkylthio group, a lower alkanoyl group, a lower alkoxycarbonyl group, a hydroxy-lower alkyl group, a hydroxy-lower alkoxyl group, a hydroxy-lower alkenyl group, a halogeno-lower alkyl group, a halogeno-lower alkoxyl group, a halogeno-lower alkenyl group, an aryl group, a heteroaryl group, an aryl-lower alkoxyl group or an aroyl group, B represents cyano group, nitro group, acetyl group, tetrazole group, triazole group or a group of the following general formula (3) or (4):

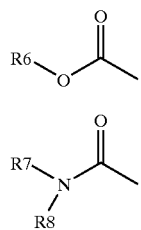
(3)

(4)

wherein $R^6$ to $R^8$ each represent hydrogen atom, a linear, branched or cyclic, saturated or unsaturated hydrocarbon group having 1 to 6 carbon atoms, an alkyl group substituted with a cyclic alkyl group which may contain a hetero atom, a substituted or unsubstituted aryl group, a substituted or unsubstituted heteroaryl group, a hydroxy-lower alkyl group, a hydroxy-lower alkenyl group, a halogeno-lower alkyl group, a halogeno-lower alkenyl group, an aryl-lower alkyl group, an aryl-lower alkenyl group, a heteroaryl-lower alkyl group (excluding pyridine-3-ylpropyl group), a heteroaryl-lower alkenyl group, a cyano-lower alkyl group or a cyano-lower alkenyl group, and the chains of $R^6$ to $R^8$ may contain a hetero atom, or $R^7$ and $R^8$ may together form a ring which may contain a hetero atom, C represents hydrogen atom, a lower alkyl group, dimethoxymethyl group, cyano group, a hydroxy-lower alkyl group, a halogeno-lower alkyl group (C does not represent these groups listed above when E represents hydrogen atom, a lower alkyl group, dimethoxymethyl group, cyano group, a hydroxy-lower alkyl group or a halogeno-lower alkyl group), a substituted or unsubstituted amino-lower alkyl group (the substituent represents hydrogen atom or a lower alkyl group, and if necessary, they may contain a hetero atom in the chain thereof), an azido-lower alkyl group, an aryl group, a heteroaryl group, an aryl-lower alkyl group, a heteroaryl-lower alkyl group or a lower alkyl group substituted with a cyclic alkyl group which may contain a hetero atom in the group, D represents hydrogen atom, a lower alkyl group, a hydroxy-lower alkyl group or an aryl-lower alkyl group, E represents hydrogen atom, a lower alkyl group, dimethoxymethyl group, cyano group, a hydroxy-lower alkyl group, a halogeno-lower alkyl group (E does not represent these groups listed above when C represents hydrogen atom, a lower alkyl group, dihydropyridine group, cyano group, a hydroxy-lower alkyl group or a halogeno-lower alkyl group), a substituted or unsubstituted amino-lower alkyl group (the substituent represents hydrogen atom or a lower alkyl group, and if necessary, they may contain a hetero atom in the chain thereof), an azido-lower alkyl group, an aryl group, a heteroaryl group, an aryl-lower alkyl group, a heteroaryl-lower alkyl group or a lower alkyl group substituted with a cyclic alkyl group which may contain a hetero atom in the group, F represents an aryl group, a heteroaryl group or a cyclic alkyl group which may contain a hetero atom in the group, excluding piperidinyl group and piperazinyl group, G represents hydrogen atom or a lower alkyl group, $X_1$ represents an interatomic bond, $-CH_2-$, $-CH_2CH_2-$, $-CH=CH-$ or $-C\equiv C-$, and Y represents a group represented by any of the following general formulae (5) to (14):

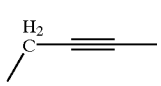
(5)

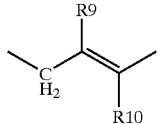
(6)

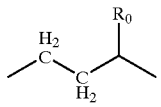
(7)

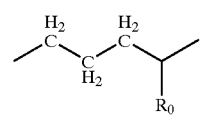
(8)-1

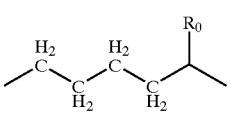
(8)-2

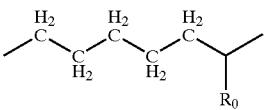
(8)-3

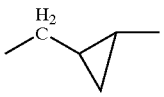
(9)

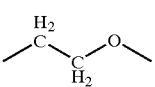
(10)

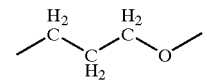
(11)

-continued

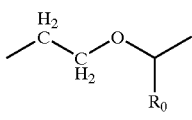
(12)

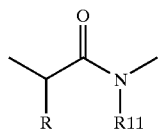
(13)

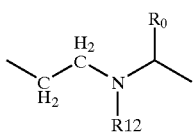
(14)

wherein $R^9$ to $R^{12}$, R and $R^0$ may the same or different from each other, and they each represent hydrogen atom, a lower alkyl group, a hydroxy-lower alkyl group, a thio-lower alkyl group, an alkylthio-lower alkyl group, an aryl group, an aryl-lower alkyl group or a heteroaryl-lower alkyl group, B and C may together form a lactone ring or a lactam ring, two of $R^1$ to $R^3$ may be bonded together to form a ring, $R^9$ and $R^{10}$ may be bonded together to form a ring, and $R^0$ may be condensed with F to form a ring.

The present invention also provides an N-type calcium channel antagonist containing a dihydropyridine derivative of above general formula (1-1) or a pharmaceutically acceptable salt thereof as an active ingredient.

The present invention further provides a therapeutic agent containing the dihydropyridine derivative represented by the following general formula (1-1) or a pharmaceutically acceptable salt thereof as the active ingredient, for any of acute stage of ischemic cerebrovascular disorders caused by cerebral infarction or intracerebral bleeding, Alzheimer's disease, AIDS related dementia, Parkinson's disease, progressive neurodegenerative diseases, neuropathy caused by head injury, pain caused by thromboangiitis obliterans, postoperative pain, migraine, visceral pain, bronchial asthma, unstable angina, irritable colitis and withdrawal symptoms after addiction to drugs:

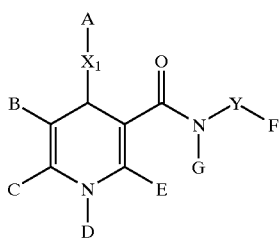
(1-1)

wherein

A represents a group of the following general formula (2), or 1-naphthyl, 2-naphthyl, thiophene-3-yl, thiophene-2-yl, furan-3-yl, furan-2-yl, pyridine-4-yl, pyridine-3-yl, pyridine-2-yl, indole-2-yl or indole-3-yl group:

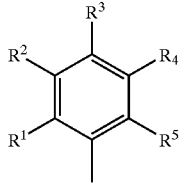
(2)

wherein $R^1$, $R^2$, $R^3$, $R^4$ and $R^5$ may be the same or different from each other and each represent hydrogen atom, a halogen atom, hydroxyl group, carboxyl group, amino group, cyano group, nitro group, a lower alkyl group, a lower alkoxyl group, a lower alkenyl group, a lower alkynyl group, a lower alkylamino group, a lower alkylthio group, a lower alkanoyl group, a lower alkoxycarbonyl group, a hydroxy-lower alkyl group, a hydroxy-lower alkoxyl group, a hydroxy-lower alkenyl group, a halogeno-lower alkyl group, a halogeno-lower alkoxyl group, a halogeno-lower alkenyl group, an aryl group, a heteroaryl group, an aryl-lower alkoxyl group or an aroyl group, B represents cyano group, nitro group, acetyl group, tetrazole group, triazole group or a group of the following general formula (3) or (4):

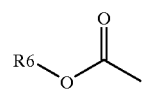
(3)

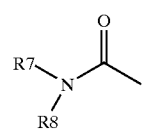
(4)

wherein $R^6$ to $R^8$ each represent hydrogen atom, a linear, branched or cyclic, saturated or unsaturated hydrocarbon group having 1 to 6 carbon atoms, an alkyl group substituted with a cyclic alkyl group which may contain a hetero atom, a substituted or unsubstituted aryl group, a substituted or unsubstituted heteroaryl group, a hydroxy-lower alkyl group, a hydroxy-lower alkenyl group, a halogeno-lower alkyl group, a halogeno-lower alkenyl group, an aryl-lower alkyl group, an aryl-lower alkenyl group, a heteroaryl-lower alkyl group (excluding pyridine-3-ylpropyl group), a heteroaryl-lower alkenyl group, a cyano-lower alkyl group or a cyano-lower alkenyl group, and the chains of $R^6$ to $R^8$ may contain a hetero atom, or $R^7$ and $R^8$ may together form a ring which may contain a hetero atom, C represents hydrogen atom, a lower alkyl group, dimethoxymethyl group, cyano group, a hydroxy-lower alkyl group, a halogeno-lower alkyl group, an amino-lower alkyl group, an azido-lower alkyl group, an aryl group, a heteroaryl group, an aryl-lower alkyl group, a heteroaryl-lower alkyl group (C does not represent these groups listed above when E represents hydrogen atom, a lower alkyl group, dimethoxymethyl group, cyano group, a hydroxy-lower alkyl group, a halogeno-lower alkyl group, an amino-lower alkyl group, an azido-lower alkyl group, an aryl group, a heteroaryl group, an aryl-lower alkyl group or a heteroaryl-lower alkyl group), a monosubstituted amino-lower alkyl group wherein the substituent represents a lower alkyl group, a disubstituted amino-lower alkyl group wherein the substituents represent the same or different lower alkyl groups, or a lower alkyl group substituted with a cyclic alkyl group which may contain a hetero atom in the group, D represents hydrogen atom, a lower alkyl group, a hydroxy-lower alkyl group or an aryl-lower alkyl group, E represents hydrogen atom, a lower alkyl group, dimethoxymethyl group, cyano group, a hydroxy-lower alkyl group, a halogeno-lower alkyl group, an amino-lower alkyl group, an azido-lower alkyl group, an aryl group, a heteroaryl group, an aryl-lower alkyl group, a heteroaryl-lower alkyl group (E does not represent these groups listed above when C represents hydrogen atom, a lower alkyl group, dimethoxymethyl group, cyano group, a hydroxy-lower alkyl group, a halogeno-lower alkyl group, an amino-lower alkyl group, an azido-lower alkyl group, an aryl group, a heteroaryl group, an aryl-lower alkyl group or a heteroaryl-lower alkyl group), a monosubstituted amino-lower alkyl group wherein the substituent represents a lower alkyl group, a disubstituted amino-lower alkyl group wherein the substituents represent the same or different lower alkyl groups, or a lower alkyl group substituted with a cyclic alkyl group which may contain a hetero atom in the group, F represents an aryl group, a heteroaryl group or a cyclic alkyl group which may contain a hetero atom in the group, excluding piperidinyl group and piperazinyl group, G represents hydrogen atom or a lower alkyl group, $X_1$ represents an interatomic bond, $-CH_2-$, $-CH_2CH_2-$, $-CH=CH-$ or $-C\equiv C-$, and Y represents a group represented by any of the following general formulae (5) to (14):

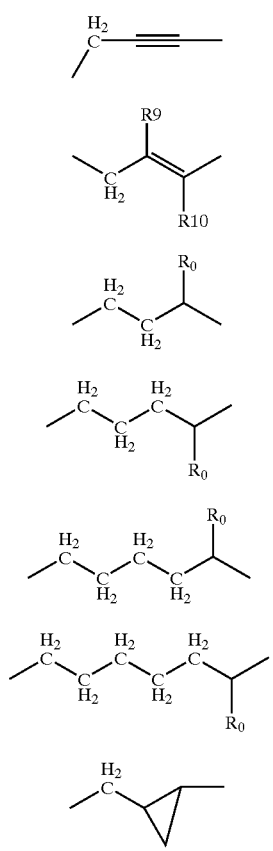

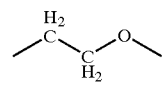

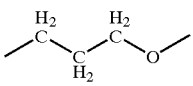

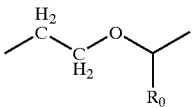

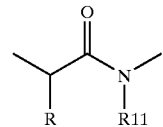

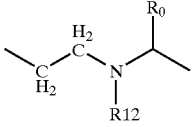

wherein $R^9$ to $R^{12}$, R and $R^0$ may the same or different from each other, and they each represent hydrogen atom, a lower alkyl group, a hydroxy-lower alkyl group, a thio-lower alkyl group, an alkylthio-lower alkyl group, an aryl group, an aryl-lower alkyl group or a heteroaryl-lower alkyl group, B and C may together form a lactone ring or a lactam ring, two of $R^1$ to $R^3$ may be bonded together to form a ring, $R^9$ and $R^{10}$ may be bonded together to form a ring, and $R^0$ may be condensed with F to form a ring.

The present invention also provides a pharmaceutical composition containing the dihydropyridine derivative represented by the above general formula (1) or a pharmaceutically acceptable salt thereof, a carrier and/or a diluent.

BEST MODE FOR CARRYING OUT THE INVENTION

The term "lower" herein indicates that the group has 1 to 6 carbon atoms. Alkyl groups themselves and also alkyl groups in alkoxyl groups, alkenyl groups, alkylamino groups, alkylthio groups and alkanoyl groups may be either linear or branched. Examples of these alkyl groups are methyl group, ethyl group, propyl group, isopropyl group, butyl group, secondary and tertiary butyl groups, pentyl group and hexyl group. Among them, those having 1 to 3 carbon atoms are preferred. The aryl-lower alkyl groups include, for example, benzyl group. The heteroaryl-lower alkyl groups include, for example, pyridylmethyl group. The aryl-lower alkoxyl groups include, for example, benzyloxy group. The halogen atoms include fluorine, chlorine, bromine and iodine atoms. In the present specification, the aryl groups are both substituted and unsubstituted aryl groups. They are preferably phenyl group and substituted phenyl group, and the substituents are particularly preferably halogens, alkyl groups and alkoxyl groups. The heteroaryl groups are substituted or unsubstituted heteroaryl groups such as, preferably, pyridyl group, furyl group, substituted pyridyl groups and substituted furyl groups. Halogens, alkyl groups and alkoxyl groups are particularly preferred as the substituents. The aroyl groups include, for example, benzoyl group and pyridylcarbonyl group.

In the present invention, the amino-lower alkyl groups indicate unsubstituted amino-lower alkyl groups, and the unsubstituted or substituted amino-lower alkyl groups indicate unsubstituted, monosubstituted or disubstituted amino-lower alkyl groups.

1-Naphthyl group, 2-naphthyl group, indole-2-yl group and indole-3-yl group represented by A in the above general formulae (1) and (1-1) are either unsubstituted or substituted. The substituents are those listed above for $R^1$ to $R^5$.

Thiophene-3-yl group, thiophene-2-yl group, furan-3-yl group, furan-2-yl group, pyridine-4-yl group, pyridine-3-yl group and pyridine-2-yl group represented by A are also either unsubstituted or substituted. When two or more substituents are contained therein, they may form a ring together. The substituents are those described above with reference to 1-naphthyl group or the like. The rings formed by those groups include benzothiophene, benzofuran, quinoline, isoquinoline, etc.

A is preferably a group represented by the general formula (2). In these groups, those wherein one or two of $R^1$ to $R^5$ represent a halogen atom, particularly chlorine atom are preferred. Particularly preferably, $R^4$ represents chlorine atom, and $R^1$ to $R^3$ and $R^5$ each represent hydrogen atom.

The substituents in the substituted or un-substituted aryl groups and substituted or un-substituted heteroaryl groups represented by $R^6$ to $R^8$ in the groups represented by general formula (3) or (4) in groups B in above general formulae (1) and (1-1) are, for example, halogen atoms (such as fluorine, chlorine, bromine and iodine atoms), hydroxyl group, carboxyl group, amino group, cyano group, nitro group, lower alkyl groups, lower alkoxyl groups, halogeno-lower alkyl groups and lower alkoxycarbonyl groups.

The groups represented by B are preferably carboxyl group, carbamoyl group which may have a substituent, cyano group and lower alkoxycarbonyl (such as methoxycarbonyl) groups. Carboxyl group and carbamoyl group which may have a substituent are more preferred.

The lower alkyl groups, hydroxy-lower alkyl groups, halogeno-lower alkyl groups, substituted or unsubstituted amino-lower alkyl groups, azido-lower alkyl groups, aryl groups, heteroaryl groups, aryl-lower alkyl groups, heteroaryl-lower alkyl groups and lower alkyl groups substituted with a cyclic alkyl group which may contain a hetero atom in the ring thereof may contain a hetero atom in their chains. The hetero atoms include, for example, oxygen, nitrogen and sulfur atoms. The groups containing such a hetero atom in the chain include, for example, hydroxyethoxymethyl group, methoxymethyl group, methoxyethyl group, chloroethoxymethyl group, aminoethoxymethyl group, monomethylaminoethoxymethyl group, dimethylaminoethoxymethyl group, azidoethoxymethyl group, methylthioethyl group, phenylethoxymethyl group, 2-pyridylethoxymethyl group, 3-pyridylethoxymethyl group, 4-pyridylethoxymethyl group, cyclohexylethoxymethyl group and piperidine-1-ylethoxymethyl group.

C and E in the general formula (1) are each preferably a lower alkyl group, a substituted or unsubstituted amino-lower alkyl group, an aryl-lower alkyl group, a heteroaryl-lower alkyl group or a lower alkyl group substituted with a cyclic alkyl group (containing or not containing a hetero atom in the ring), and they may contain a hetero atom in the chain thereof. More preferably, they are each an aryl-lower alkyl group or a lower alkyl group substituted with a cyclic alkyl group (containing or not containing a hetero atom in the ring), and they may contain a hetero atom in the chain thereof. Preferred examples of them include methyl group, methoxymethyl group, aminoethoxymethyl group, dimethylaminoethoxymethyl group, phenylethoxymethyl group, 2-pyridylethoxymethyl group, cyclohexylethoxymethyl group and piperidine-1-ylethoxymethyl group. Among them, methyl group, methoxymethyl group, aminoethoxymethyl group, phenylethoxymethyl group and cyclohexylethoxymethyl group are more preferred.

The lower alkyl groups, hydroxy-lower alkyl groups, halogeno-lower alkyl groups, amino-lower alkyl groups, azido-lower alkyl groups, aryl-lower alkyl groups, heteroaryl-lower alkyl groups, mono-substituted amino-lower alkyl groups, disubstituted amino-lower alkyl groups and lower alkyl groups substituted with a cyclic alkyl group which may contain a hetero atom in the ring, which are represented by C or E in the above general formula (1-1) may contain, if necessary, a hetero atom in the chain thereof. The hetero atoms include, for example, oxygen, nitrogen and sulfur atoms. The groups containing such a hetero atom in the chain include, for example, hydroxyethoxymethyl group, methoxymethyl group, methoxyethyl group, chloroethoxymethyl group, aminoethoxymethyl group, monomethylaminoethoxymethyl group, dimethylaminoethoxymethyl group, azidoethoxymethyl group, methylthioethyl group, phenylethoxymethyl group, 2-pyridylethoxymethyl group, 3-pyridylethoxymethyl group, 4-pyridylethoxymethyl group, cyclohexylethoxymethyl group and piperidine-1-ylethoxymethyl group.

C and E in the general formula (1-1) are each preferably a lower alkyl group, a substituted or unsubstituted amino-lower alkyl group or a lower alkyl group substituted with a cyclic alkyl group (containing or not containing a hetero atom in the ring), and they may contain a hetero atom in the chain thereof. More preferably, they are each an aryl-lower alkyl group or a lower alkyl group substituted with a cyclic alkyl group (containing or not containing a hetero atom in the ring), and they may contain a hetero atom in the chain thereof. Preferred examples of them include methyl group, methoxymethyl group, aminoethoxymethyl group, dimethylaminoethoxymethyl group, phenylethoxymethyl group, cyclohexylethoxymethyl group and piperidine-1-ylethoxymethyl group. Among them, methyl group, methoxymethyl group, aminoethoxymethyl group, phenylethoxymethyl group and cyclohexylethoxymethyl group are more preferred.

D in the above general formulae (1) and (1-1) is preferably hydrogen atom.

F in the above general formulae (1) and (1-1) preferably represents a group of the following general formula (15), thiophene-3-yl group, thiophene-2-yl group, furan-3-yl group, furan-2-yl group, pyridine-4-yl group, pyridine-3-yl group, pyridine-2-yl group, cyclohexyl group, morpholine-4-yl group, imidazole-1-yl group or pyrrolidinone-1-yl group.

F more preferably represents a group of the general formula (15) or morpholine-4-yl group. Those represented by the general formula (15) such as phenyl group are particularly preferred.

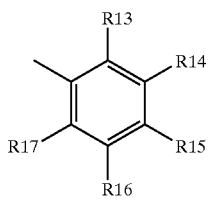

(15)

wherein $R^{13}$, $R^{14}$, $R^{15}$, $R^{16}$ and $R^{17}$ may be the same or different from each other and each represent hydrogen atom, a halogen atom, hydroxyl group, carboxyl group, amino group, cyano group, nitro group, a lower alkyl group, a lower alkoxyl group, a lower alkenyl group, a lower alkynyl group, a lower alkylamino group, a lower alkylthio group, a lower alkanoyl group, a hydroxy-lower alkyl group, a hydroxy-lower alkoxyl group, a hydroxy-lower alkenyl group, a halogeno-lower alkyl group, a halogeno-lower alkoxyl group, a halogeno-lower alkenyl group, an aryl-lower alkyl group, an aryl-lower alkoxyl group, a lower alkoxycarbonyl group, carbamoyl group which may have a substituent, a carboxyamido group which may have a substituent, an aroyl group, an aryl group, a heteroaryl group or a saturated cyclic hydrocarbon group having 3 to 8 carbon atoms, they may contain a hetero atom in the chains thereof, and two of $R^{13}$ to $R^{15}$ may be bonded together to form a ring.

Thiophene-3-yl group, thiophene-2-yl group, furan-3-yl group, furan-2-yl group, pyridine-4-yl group, pyridine-3-yl group, pyridine-2-yl group and cyclohexyl group may be either unsubstituted or substituted. When they contain two or more substituents, these substituents may together form a ring. The substituents are those listed above with reference to $R^1$ to $R^5$. The rings formed by them together are those listed above with reference to group A.

G is preferably hydrogen atom.

$X_1$ is preferably an interatomic bond.

The groups represented by Y are preferably those of general formulae (6), (7), (8)-1, (8)-2 and (8)-3 wherein $R^9$ and $R^{10}$ each represent hydrogen atom and $R^0$ represents phenyl group. When $R^0$ and F in Y are condensed to form a ring, the ring is a tricyclic group such as fluorene, dihydroanthracene, xanthene, thioxanthene, dihydroacridine or dibenzosuberane.

In the present invention, it is preferred that Y in the general formula (1) represents a group of the general formula (6).

Y in the general formula (1) preferably represents a group of any of general formulae (7), (8)-1, (8)-2 and (8)-3.

In general formula (1), C is preferably a substituted or unsubstituted amino-lower alkyl group wherein the substituent represents hydrogen atom or a lower alkyl group and it may contain a hetero atom in the chain thereof, an azido-lower alkyl group, an aryl group, a heteroaryl group, an aryl-lower alkyl group, a heteroaryl-lower alkyl groups or a lower alkyl group substituted with a cyclic alkyl group which may contain a hetero atom in the ring thereof. C is preferably a lower alkyl group.

In general formula (1), E is preferably a substituted or unsubstituted amino-lower alkyl group wherein the substituent represents hydrogen atom or a lower alkyl group and it may contain a hetero atom in the chain thereof, an azido-lower alkyl group, an aryl group, a heteroaryl group, an aryl-lower alkyl group wherein the alkyl group may contain a hetero atom, a heteroaryl-lower alkyl group wherein the alkyl group may contain a hetero atom, or a lower alkyl group (containing or not containing a hetero atom) substituted with a cyclic alkyl group which may contain a hetero atom in the group thereof. E is preferably a lower alkyl group.

It is preferred that in general formula (1), D represents hydrogen atom, G represents hydrogen atom, $X_1$ represents an interatomic bond and Y represents a group of general formula (6) wherein $R^9$ and $R^{10}$ each represent hydrogen atom.

It is also preferred that in general formula (1), D represents hydrogen atom, G represents hydrogen atom, $X_1$ represents an interatomic bond and Y represents a group of any of general formulae (7), (8)-1, (8)-2 and (8)-3.

It is further preferred that in general formula (1), B represents a group of general formula (3), a group of general formula (4) wherein either $R^7$ or $R^8$ represents hydrogen atom or B and C are condensed together to form a lactone ring, D represents hydrogen atom, G represents hydrogen atom, $X_1$ represents an interatomic bond and Y represents a group of general formula (6) wherein $R^9$ and $R^{10}$ each represent hydrogen atom, a group of general formula (7) or a group of general formula (8)-1, (8)-2 or (8)-3.

It is also preferred that in general formula (1), B represents a group of general formula (3), wherein $R^6$ represents hydrogen group, or a group of general formula (4) wherein either $R^7$ or $R^8$ represents hydrogen atom, D represents hydrogen atom, G represents hydrogen atom, $X_1$ represents an interatomic bond and Y represents a group of general formula (6) wherein $R^9$ and $R^{10}$ each represent hydrogen atom, a group of general formula (7) or a group of general formula (8)-1, (8)-2 or (8)-3.

It is preferred that in general formula (1), B represents a group of general formula (3), wherein $R^6$ represents hydrogen group, D represents hydrogen atom, G represents hydrogen atom, $X_1$ represents an interatomic bond and Y represents a group of general formula (6) wherein $R^9$ and $R^{10}$ each represent hydrogen atom, a group of general formula (7) or a group of general formula (8)-1, (8)-2 or (8)-3.

It is preferred that in general formula (1), B represents a group of general formula (3), C represents any of substituted or unsubstituted amino-lower alkyl groups, wherein the substituent represents hydrogen atom or a lower alkyl group and, if necessary, the chain may contain a hetero atom, an azido-lower alkyl group, an aryl group, a heteroaryl group, an aryl-lower alkyl group, a heteroaryl-lower alkyl group, wherein the alkyl group may contain a hetero atom, a lower alkyl group substituted with a cyclic alkyl group which may contain a hetero atom, D represents hydrogen atom, G represents hydrogen atom and $X_1$ represents an interatomic bond. C preferably represents a lower alkyl group.

It is preferred that in general formula (1), B represents a group of general formula (3), D represents hydrogen atom, E represents any of substituted or unsubstituted amino-lower alkyl groups, wherein the substituent represents hydrogen atom or a lower alkyl group and, if necessary, the chain may contain a hetero atom, an azido-lower alkyl group, an aryl group, a heteroaryl group, an aryl-lower alkyl group, a heteroaryl-lower alkyl group, a lower alkyl group substituted with a cyclic alkyl group which may contain a hetero atom, G represents hydrogen atom, $X_1$ represents an interatomic bond. E preferably represents a lower alkyl group.

It is preferred that in general formula (1), B represents a group of general formula (3) wherein $R^6$ represents hydrogen atom, C represents an aryl-lower alkyl group, a heteroaryl-lower alkyl group, a lower alkyl group substituted with a cyclic alkyl group which may contain a hetero atom, D represents hydrogen atom, G represents hydrogen atom, $X_1$ represents an interatomic bond. C also preferably represents a lower alkyl group.

It is preferred that in general formula (1), B represents a group of general formula (3) wherein $R^6$ represents hydrogen atom, D represents hydrogen atom, E represents an aryl-lower alkyl group, a heteroaryl-lower alkyl group, a lower alkyl group substituted with a cyclic alkyl group which may contain a hetero atom, G represents hydrogen atom, $X_1$ represents an interatomic bond. E also preferably represents a lower alkyl group.

Preferred are dihydropyridine derivatives of the general formula (1) wherein A represents a group of the general formula (2), B represents a group of the general formula (3), wherein $R^6$ represents hydrogen atom, D represents hydrogen atom, F represents a group of the general formula (15), G represents hydrogen atom, $X_1$ represents an interatomic bond, Y represents a group of general formula (6) wherein $R^9$ and $R^{10}$ each represent hydrogen atom, a group of general formula (7) or a group of general formula (8)-1, (8)-2 or (8)-3 and pharmaceutically acceptable salts thereof.

Dihydropyridine derivatives (1) of the present invention can be produced by processes described below:

For example, dihydropyridine derivatives (1-2) wherein B represents carboxyl group [$R^6$ in general formula (3) represents hydrogen atom] and D represents hydrogen atom can be produced by the following reaction scheme:

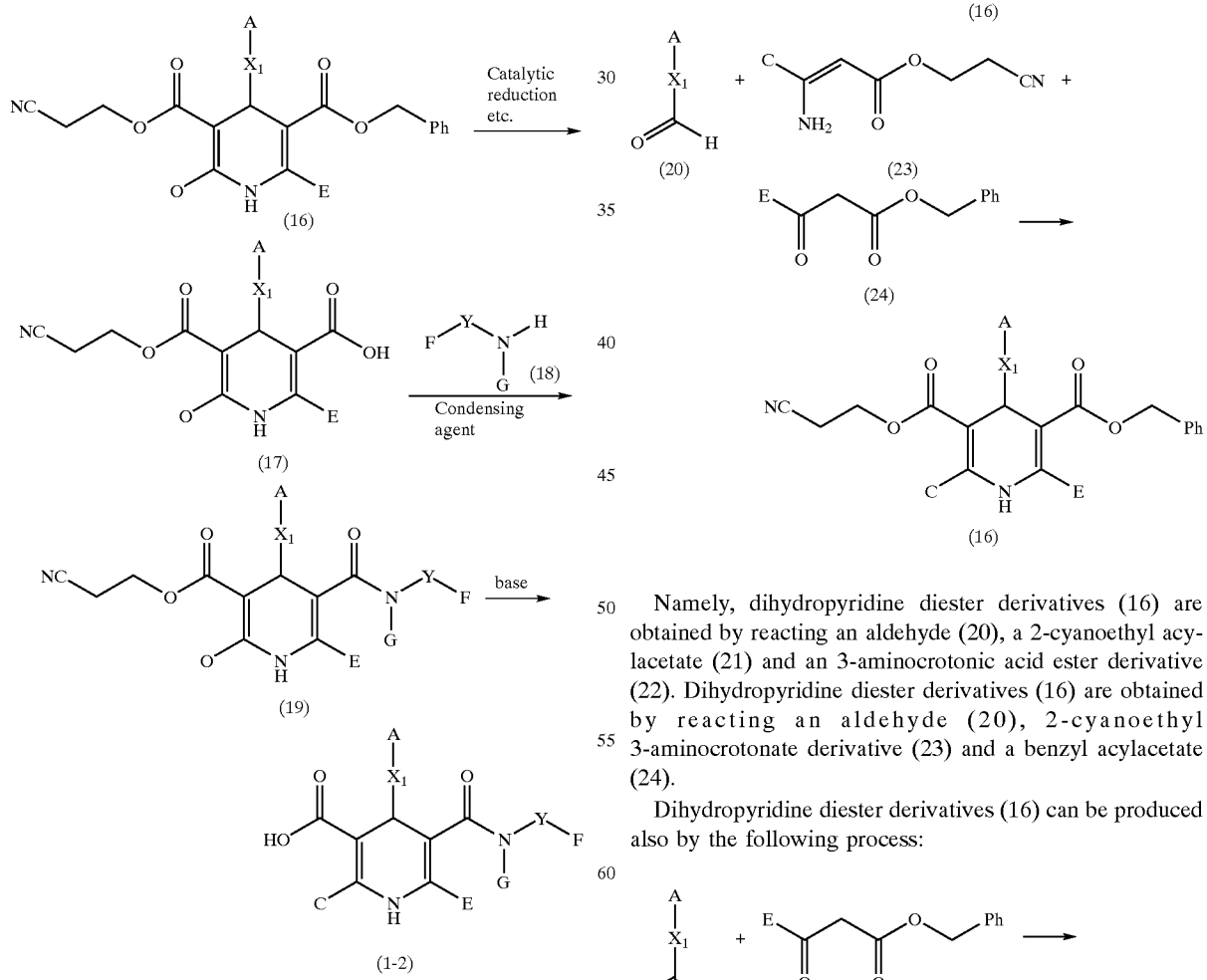

Namely, dihydropyridine derivatives (1-2) of the present invention can be produced by converting a dihydropyridine diester derivative (16) into compound (17) by, for example, catalytic reduction, condensing the obtained product with an amine (18), and treating the condensation product with a base such as sodium hydroxide.

Dihydropyridine diester derivatives (16) used in the above-described process can be produced as follows:

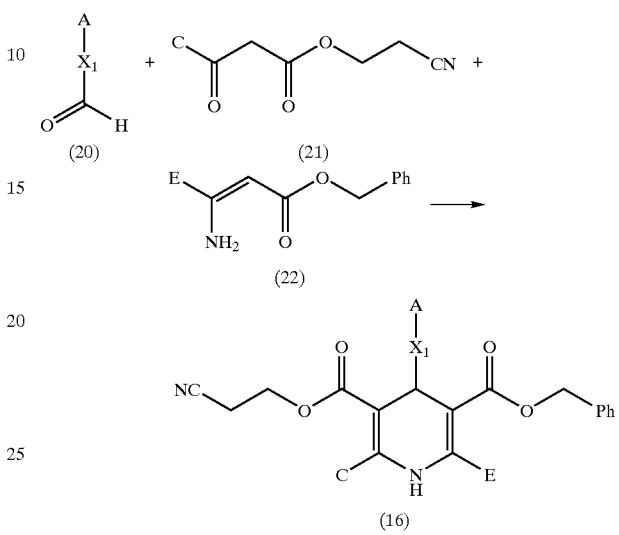

Namely, dihydropyridine diester derivatives (16) are obtained by reacting an aldehyde (20), a 2-cyanoethyl acylacetate (21) and an 3-aminocrotonic acid ester derivative (22). Dihydropyridine diester derivatives (16) are obtained by reacting an aldehyde (20), 2-cyanoethyl 3-aminocrotonate derivative (23) and a benzyl acylacetate (24).

Dihydropyridine diester derivatives (16) can be produced also by the following process:

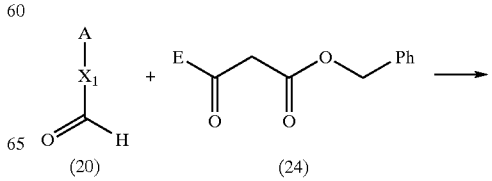

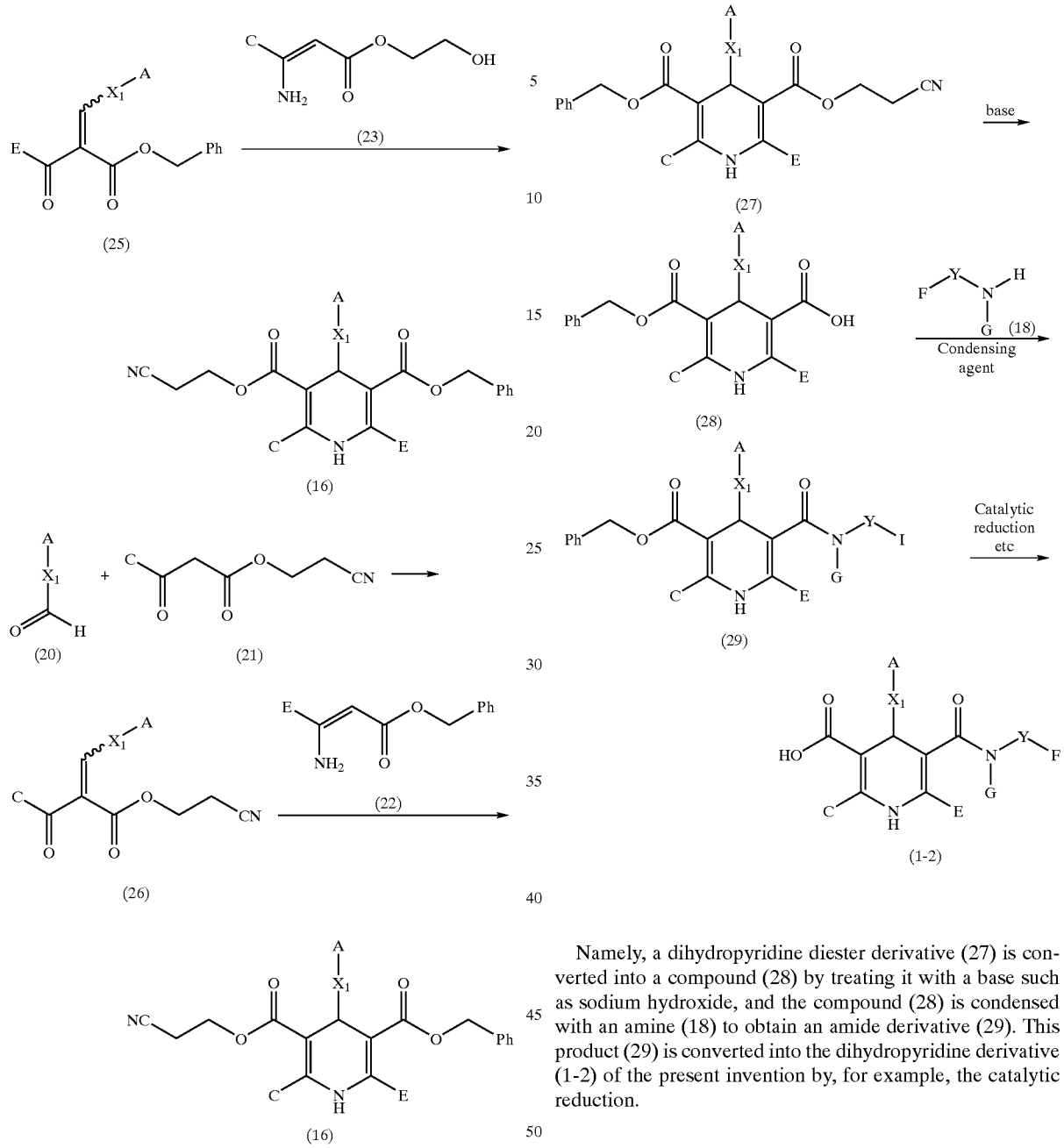

Namely, a compound (25) is obtained by Knoevenagel reaction of an aldehyde (20) and a benzyl acylacetate (24). Then the compound (25) is reacted with an 2-cyanoethyl 3-amino-crotonate derivative (23) to obtain a dihydropyridine diester derivative (16). In another process, a compound (26) obtained by Knoevenagel reaction of an aldehyde (20) and a 2-cyanoethyl acylacetate (21) is reacted with a benzyl 3-aminocrotonate derivative (22) to obtain a dihydropyridine diester derivative (16).

The dihydropyridine derivatives (1-2) can be produced also by the following reaction scheme:

Namely, a dihydropyridine diester derivative (27) is converted into a compound (28) by treating it with a base such as sodium hydroxide, and the compound (28) is condensed with an amine (18) to obtain an amide derivative (29). This product (29) is converted into the dihydropyridine derivative (1-2) of the present invention by, for example, the catalytic reduction.

The dihydropyridine diester derivative (27) used in the above-described process can be produced by the same process as that employed for the production of the dihydropyridine diester derivative (16).

The dihydropyridine derivatives (1-2) can be produced as follows:

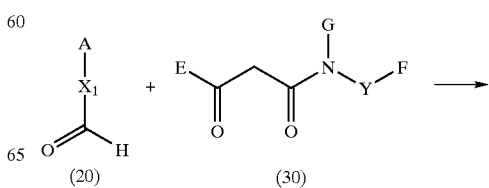

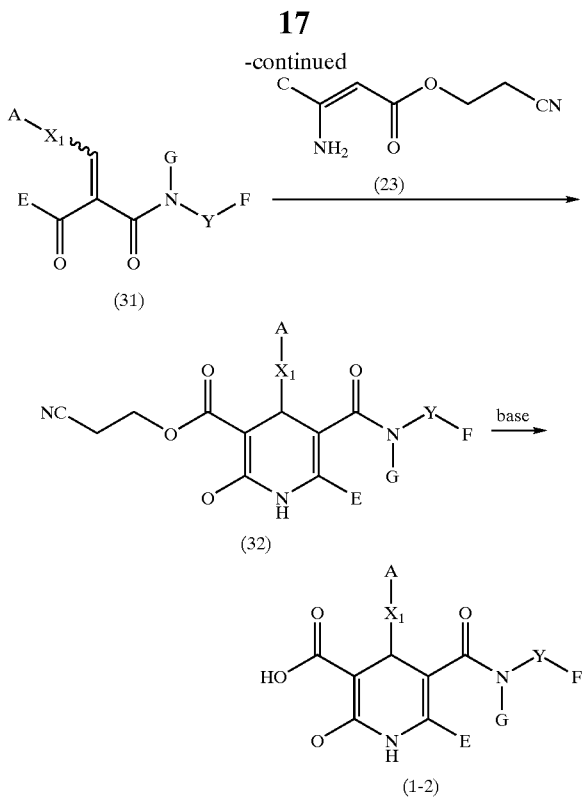

Namely, a compound (32) is obtained by subjecting an aldehyde (20) and an acylacetic acid amide derivative (30) to Knoevenagel reaction, and reacting the obtained compound (31) with a 2-cyanoethyl 3-aminocrotonate derivative (23) to obtain a compound (32). This product is treated with a base such as sodium hydroxide to obtain a dihydropyridine derivative (1-2) of the present invention. The compound (32) can be obtained also by directly reacting the aldehyde (20), the acylacetic acid amide derivative (30) and the 2-cyanoethyl 3-aminocrotonate derivative (23).

Dihydropyridine derivatives (1-3) of the above formula wherein B represents an ester group [$R^6$ in general formula (3) represents a substituent excluding hydrogen atom] and D represents hydrogen atom can be produced as follows:

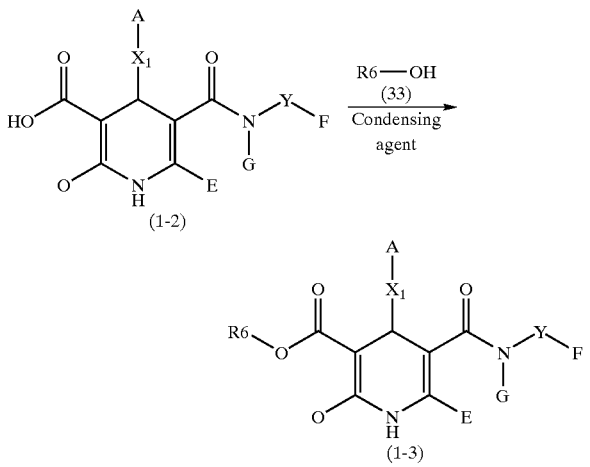

Namely, the dihydropyridine derivatives (1-3) of the present invention can be produced by condensing the dihydropyridine derivative (1-2), synthesized by the process described above, with an alcohol (33).

Dihydropyridine derivatives (1-4) of the above formula wherein B represents a substituted carbamoyl group of general formula (4) and D represents hydrogen atom can be produced as follows:

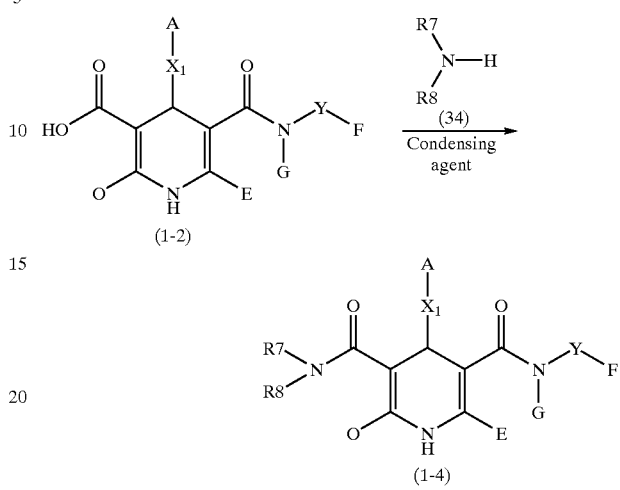

Namely, the dihydropyridine derivatives (1-4) of the present invention can be produced by condensing the dihydropyridine derivative (1-2), synthesized by the process described above, with a substituted amine (34).

Dihydropyridine derivatives (1-5) of the above formula wherein B represents cyano group and D represents hydrogen atom can be produced as follows:

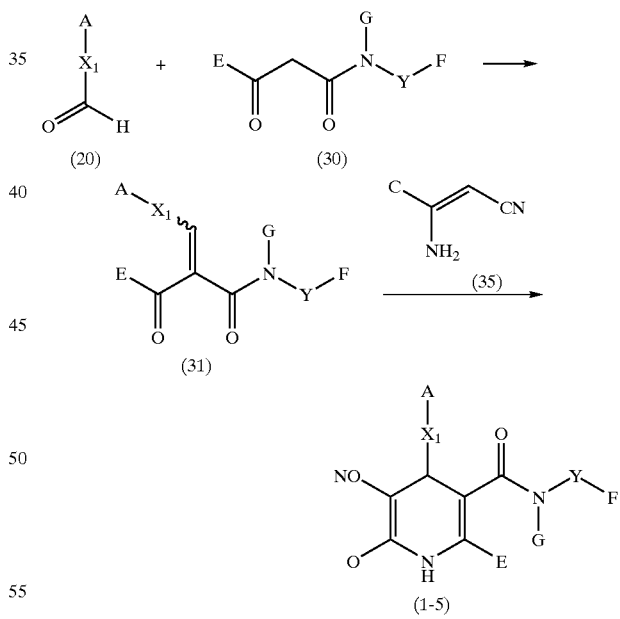

Namely, the dihydropyridine derivatives (1-5) of the present invention can be produced by reacting a compound (31), obtained by Knoevenagel reaction of the aldehyde (20) and an acylacetic acid amide derivative (30), with a 3-aminocrotonitrile derivative (35).

Dihydropyridine derivatives (1) containing an amine as the substituent of C or E can be obtained by using a halogen atom-containing compound, carrying out the reaction steps, converting the halogen atom-containing product into an azide with sodium azide or the like in the final step or the step preceding to the final step and reducing the obtained product into a primary amino group-containing derivative thereby by the hydrogenation or the like. The dihydropyridine derivatives (1) containing an amine as the substituent of C or E can be also obtained by reacting the halogen atom with a corresponding amine.

Benzyl acylacetates (24) used as the starting material can be produced as follows:

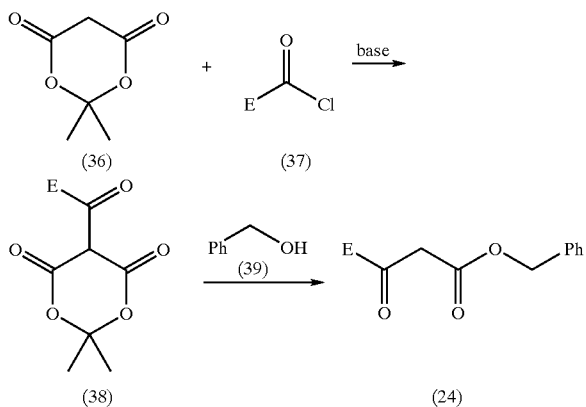

Namely, benzyl acylacetates (24) can be obtained by reacting Meldrum's acid (36) with an acyl chloride (37) in the presence of a proper base to obtain a compound (38) and then reacting the obtained compound (38) with benzyl alcohol (39).

Benzyl acylacetates (24) can also be produced as follows:

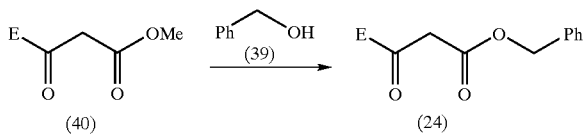

Namely, benzyl acylacetates (24) can be obtained by the transesterification of a methyl acylacetate (40) and benzyl alcohol (39).

Optical isomers of 1,4-dihydropyridines represented by general formula (1) or (1-1) are possible because they have an asymmetric carbon atom. The compounds of the present invention also include those optical isomers.

When the compounds of general formula (1) can form salts thereof, the salts are pharmaceutically acceptable ones such as ammonium salts, salts thereof with alkali metals, e.g. sodium and potassium, salts thereof with alkaline earth metals, e.g. calcium and magnesium, salts thereof with aluminum and zinc, salts thereof with organic amines, e.g. morpholine and piperidine, and salts thereof with basic amino acids, e.g. arginine and lysine.

The compounds of general formula (1) and salts thereof are administered as they are or in the form of various medicinal compositions to patients. The dosage forms of the medicinal compositions are, for example, tablets, powders, pills, granules, capsules, suppositories, solutions, sugar-coated tablets and depots. They can be prepared with ordinary preparation assistants by an ordinary method.

For example, the tablets are prepared by mixing the dihydropyridine derivative, the active ingredient of the present invention, with any of known adjuvants such as inert diluents, e.g. lactose, calcium carbonate and calcium phosphate; binders, e.g. acacia, corn starch and gelatin; extending agents, e.g. alginic acid, corn starch and pre-gelatinized starch; sweetening agents, e.g. sucrose, lactose and saccharin; corrigents, e.g. peppermint, and cherry; and lubricants, e.g. magnesium stearate, talc and carboxymethyl cellulose.

The N-type calcium channel inhibitor containing one of the compounds of above general formula (1-1) or one of salts thereof as active ingredient is usable as a therapeutic agent for various diseases, for example, acute stage of ischemic cerebrovascular disorders caused by cerebral infarction or intracerebral bleeding (including subarachnoidal hemorrhage); progressive neurodegenerative diseases such as Alzheimer's disease, AIDS related dementia and Parkinson's disease, dementia due to cerebrovascular disorder and ALS; neuropathy caused by head injury; various pains such as pain caused by spinal injury, diabetes or thromboangiitis obliterans, postoperative pain, migraine and visceral pain; various diseases associated with psychogenic stress such as bronchial asthma, unstable angina and irritable colitis; emotional disorder withdrawal symptoms after addiction to drugs such as ethanol addiction withdrawal symptoms.

The dose of the compound of general formula (1) or salt thereof used for the above-described purpose varies depending on the intended therapeutic effect, administration method, period of the treatment, and age and body weight of the patient. The dose is usually 1 µg to 5 g a day for adults in the oral administration, and 0.01 µg to 1 g a day for adults in the parenteral administration.

The following Examples will further illustrate the present invention, which are only preferred embodiments of the invention and which by no means limit the invention.

EXAMPLE 1

Synthesis of 4-(3-chlorophenyl)-6-(2-cyclohexylethoxymethyl)-5-(3,3-diphenylpropylcarbamoyl)-2-methyl-1,4-dihydropyridine-3-carboxylic acid:

1) Synthesis of Benzyl 4-(2-cyclohexylethoxy)acetoacetate 0.68 g (17.0 mmol) of sodium hydride (60% oily) was suspended in 7 ml of THF. 1.36 g (10.6 mmol) of 2-cyclohexylethanol was added to the obtained suspension at 0° C., and they were stirred at 40° C. for 30 minutes. 2.00 g (8.82 mmol) of benzyl 4-chloroacetoacetate was added to the obtained mixture at room temperature, and they were refluxed at 100° C. for 3 hours. 1 N hydrochloric acid was added to the reaction mixture. After the extraction with ethyl acetate, the organic layer was washed with 10% aqueous sodium hydroxide solution and saturated aqueous sodium chloride solution, dried over anhydrous magnesium sulfate and concentrated under reduced pressure. The residue was purified by the silica gel chromatography (hexane/ethyl acetate=4/1) to obtain the title compound.

Yield: 1.20 g (3.77 mmol) (42.7%) MS (ESI, m/z) 318 (M+H)+1H-NMR (CDCl3): 0.81–0.98 (2H, m), 1.10–1.30 (3H, m), 1.36 (1H, m), 1.46 (2H, q), 1.70–1.66 (5H, m), 3.47 (2H, t), 3.58 (2H, s), 4.05 (2H, s), 5.17 (2H, s), 7.26–7.37 (5H, m)

2) Synthesis of 3-benzyl 5-(2-cyanoethyl) 4-(3-chlorophenyl)-2-(2-cyclohexylethoxymethyl)-6-methyl-1,4-dihydropyridine-3,5-dicarboxylate 0.50 g (1.57 mmol) of benzyl 4-(2-cyclohexylethoxy) acetoacetate, 0.22 g (1.57 mmol) of 3-chlorobenzaldehyde and 0.24 g (1.57 mmol) of 2-cyanoethyl 3-aminocrotonate were stirred in 8 ml of 2-propanol under heating at 70° C. for 22 hours. After 2-propanol was evaporated under reduced pressure, the residue was purified by the silica gel chromatography (hexane/ethyl acetate=1/2) to obtain the title compound.

Yield: 0.37 g (0.64 mmol) (40.8%) MS (ESI, m/z) 577 (M+H)+1H-NMR (CDCl3): 0.88–1.05 (2H, m), 1.15–1.25

(3H, m), 1.38 (1H, m), 1.51 (2H, q), 1.60–1.78 (5H, m), 2.38 (3H, s), 2.60 (2H, t), 3.47 (2H, m), 4.24 (2H, m), 4.61 (1H, d), 4.70 (1H, d), 4.98 (1H, s), 5.02 (1H, d), 5.13 (1H, d), 7.11–7.36(10H, m)

3) Synthesis of 5-(2-cyanoethyl) 4-(3-chlorophenyl)-2-(2-cyclohexylethoxymethyl)-6-methyl-1,4-dihydropyridine-3,5-dicarboxylate:

6 ml of ethyl acetate and 10% palladium carbon were added to 0.37 g (0.64 mmol) of 3-benzyl 5-(2-cyanoethyl) 4-(3-chlorophenyl)-2-(2-cyclohexylethoxymethyl)-6-methyl-3,5-dicarboxylate, and they were stirred at room temperature in hydrogen atmosphere under normal pressure for 48 hours. The reaction mixture was filtered, and the filtrate was evaporated under reduced pressure to obtain the title compound.

Yield: 0.25 g (0.51 mmol) (80.1%) MS (ESI, m/z) 485 (M–H)–1H-NMR (CDCl3): 0.89–1.03 (2H, m), 1.20–1.26 (3H, m), 1.40 (1H, m), 1.57 (2H, q), 1.60–1.78 (5H, m), 2.40 (3H, s), 2.64 (2H, t), 3.61 (2H, m), 4.25 (2H, m), 4.61 (1H, d), 4.70 (1H, d), 4.96 (1H, s), 7.11–7.29 (4H, m), 7.34 (1H, s)

4) Synthesis of 2-cyanoethyl 4-(3-chlorophenyl)-6-(2-cyclohexylethoxymethyl)-5-(3,3-diphenylpropylcarbamoyl)-2-methyl-1,4-dihydropyridine-3-carboxylate:

0.25 g (0.51 mmol) of 5-(2-cyanoethyl) 4-(3-chlorophenyl)-2-(2-cyclohexylethoxymethyl)-6-methyl-1,4-dihydropyridine-3,5-dicarboxylate, 0.12 g (0.63 mmol) of WSC hydrochloride and 0.13 g (0.62 mmol) of 3,3-diphenylpropylamine were stirred together in 5 ml of dichloromethane at room temperature for 16 hours. 0.1 N hydrochloric acid was added to the reaction mixture. After the extraction with dichloromethane, the organic layer was concentrated under reduced pressure. The residue was purified by the silica gel chromatography (hexane/ethyl acetate=1/1) to obtain the title compound.

Yield: 0.25 g (0.37 mmol) (71.6%) MS (ESI, m/z) 680 (M+H)+1H-NMR (CDCl3): 0.86–1.00 (2H, m), 1.18–1.26 (3H, m), 1.38 (1H, m), 1.58 (2H, q), 1.60–1.78 (5H, m), 2.15 (2H, m), 2.34 (3H, s), 2.68 (2H, t), 3.11 (2H, m), 3.58 (2H, m), 3.69 (1H, t), 4.31 (2H, m), 4.70 (2H, s), 4.74 (1H, s), 5.53 (1H, t), 7.09–7.26 (14H, m), 7.31 (1H, s)

5) Synthesis of 4-(3-chlorophenyl)-6-(2-cyclohexylethoxymethyl)-5-(3,3-diphenylpropylcarbamoyl)-2-methyl-1,4-dihydropyridine-3-carboxylic acid:

0.25 g (0.37 mmol) of 2-cyanoethyl 4-(3-chlorophenyl)-6-(2-cyclohexylethoxymethyl)-5-(3,3-diphenylpropylcarbamoyl)-2-methyl-1,4-dihydropyridine-3-carboxylate was dissolved in 5 ml of methanol. 0.73 ml of 1 N aqueous sodium hydroxide solution was added to the obtained solution, and they were stirred at room temperature for 2 hours. 1 N hydrochloric acid and water were added to the reaction mixture. The precipitates thus formed were taken by the filtration and dried under reduced pressure to obtain the title compound.

Yield: 198 mg (0.32 mmol) (85.9%) MS (ESI, m/z) 626 (M–H)–1H-NMR (DMSO-d6): 0.70–0.90 (2H, m), 1.04–1.15 (3H, m), 1.25 (1H, m), 1.35 (2H, m), 1.48–1.62 (5H, m), 2.10 (2H, q), 2.25 (3H, s), 2.93 (2H, m), 3.33 (2H, m), 3.83 (1H, t), 4.22 (2H, m), 4.88 (1H, s), 7.13–7.24 (14H, m), 7.68 (1H, t), 8.30 (1H, s)

EXAMPLE 2

Synthesis of 4-(3-chlorophenyl)-5-(3,3-diphenylpropylcarbamoyl)-2-methyl-6-(2-phenylethoxymethyl)-1,4-dihydro-pyridine-3-carboxylic acid 1) Synthesis of Benzyl 4-(2-phenylethoxy)acetoacetate:

0.88 g (22.1 mmol) of sodium hydride (60% oily) was suspended in 7 ml of THF. 1.62 g (13.2 mmol) of 2-phenylethanol was added to the obtained suspension at 0° C., and they were stirred at 40° C. for 30 minutes. 2.00 g (8.82 mmol) of benzyl 4-chloroacetoacetate was added to the obtained mixture at room temperature, and they were stirred for 24 hours and then at 80° C. for 4 hours. 1 N hydrochloric acid was added to the reaction mixture. After the extraction with ethyl acetate, the organic layer was washed with 10% aqueous sodium hydroxide solution and saturated aqueous sodium chloride solution, dried over anhydrous magnesium sulfate and concentrated under reduced pressure. The residue was purified by the silica gel chromatography (hexane/ethyl acetate=4/1) to obtain the title compound.

Yield: 0.80 g (2.56 mmol) (29.0%) MS (ESI, m/z) 311 (M–H)–1H-NMR (CDCl3): 2.87 (2H, t), 3.52 (2H, s), 3.67 (2H, t), 4.07 (2H, s), 5.15 (2H, s), 7.18–7.38 (10H, m)

2) Synthesis of 5-benzyl 3-(2-cyanoethyl) 4-(3-chlorophenyl)-2-methyl-6-(2-phenylethoxymethyl)-1,4-dihydropyridine-3,5-dicarboxylate:

0.80 g (2.56 mmol) of benzyl 4-(2-phenylethoxy)acetoacetate, 0.36 g (2.56 mmol) of 3-chlorobenzaldehyde and 0.40 g (2.56 mmol) of 2-cyanoethyl 3-aminocrotonate were stirred in 5 ml of 2-propanol under heating at 80° C. for 24 hours. 2-Propanol was evaporated under reduced pressure, and the residue was purified by the silica gel chromatography (hexane/ethyl acetate=1/1) to obtain the title compound.

Yield: 0.52 g (0.91 mmol) (35.6%) MS (ESI, m/z) 569 (M–H)–1H-NMR (CDCl3): 2.09 (3H, s), 2.58 (2H, t), 2.94 (2H, t), 3.78 (2H, t), 4.21 (2H, m), 4.70 (2H, s), 4.93 (1H, s), 5.02 (1H, d), 5.13 (1H, d), 6.85 (1H, s), 7.09–7.35 (14H, m)

3) Synthesis of 3-(2-cyanoethyl) 4-(3-chlorophenyl)-2-methyl-6-(2-phenylethoxymethyl)-1,4-dihydropyridine-3,5-dicarboxylate:

The title compound was obtained from 0.52 g (0.91 mmol) of 5-benzyl 3-(2-cyanoethyl) 4-(3-chlorophenyl)-2-methyl-6-(2-phenylethoxymethyl)-1,4-dihydropyridine-3,5-dicarboxylate in the same manner as that of Example 1–3).

Yield: 0.34 g (0.71 mmol) (77.6%) MS (ESI, m/z) 479 (M–H)–1H-NMR (CDCl3): 2.09 (3H, s), 2.60 (2H, t), 2.95 (2H, t), 3.80 (2H, t), 4.23 (2H, m), 4.66 (2H, s), 4.89 (1H, s), 6.95 (1H, s), 7.12–7.35 (9H, m)

4) Synthesis of 2-cyanoethyl 4-(3-chlorophenyl)-5-(3,3-diphenylpropylcarbamoyl)-2-methyl-6-(2-phenylethoxymethyl)-1,4-dihydro-pyridine-3-carboxylate:

The title compound was obtained from 0.16 g (0.33 mmol) of 3-(2-cyanoethyl) 4-(3-chlorophenyl)-2-methyl-6-(2-phenylethoxymethyl)-1,4-dihydropyridine-3,5-dicarboxylate and 0.08 g (0.38 mmol) of 3,3-diphenylpropylamine in the same manner as that of Example 1–4).

Yield: 0.10 g (0.15 mmol) (44.6%) MS (ESI, m/z) 674 (M+H)+1H-NMR (CDCl3): 2.06 (3H, s), 2.13 (2H, m), 2.67 (2H, t), 2.94 (2H, t), 3.08 (2H, m), 3.68 (1H, t), 3.79 (2H, t), 4.30 (2H, m), 4.68 (1H, s), 4.70 (1H, d), 4.78 (1H, d), 5.47 (1H, t), 6.76 (1H, s), 7.10–7.33 (19H, m)

5) Synthesis of 4-(3-chlorophenyl)-5-(3,3-diphenylpropylcarbamoyl)-2-methyl-6-(2-phenylethoxymethyl)-1,4-dihydropyridine-3-carboxylic acid:

The title compound was obtained from 0.10 g (0.15 mmol) of 2-cyanoethyl 4-(3-chlorophenyl)-5-(3,3-diphenylpropylcarbamoyl)-2-methyl-6-(2-phenylethoxymethyl)-1,4-dihydropyridine-3-carboxylate in the same manner as that of Example 1–5).

Yield: 76.9 mg (0.12 mmol)(83.4%) MS (ESI, m/z) 619 (M−H)−1H-NMR (DMSO-d6): 2.03 (2H, q), 2.21 (3H, s), 2.77 (2H, t), 2.89 (2H, m), 3.55 (2H, m), 3.80 (1H, t), 4.22 (1H, d), 4.32 (1H, d), 4.86 (1H, s), 7.07–7.24 (19H, m), 7.56 (1H, t), 8.12 (1H, s)

EXAMPLE 3

Synthesis of 4-(3-chlorophenyl)-2-methyl-6-(2-phenylethoxymethyl)-5-(3-phenyl-2-propene-1-ylcarbamoyl)-1,4-dihydro-pyridine-3-carboxylic acid:

1) Synthesis of 2-cyanoethyl 4-(3-chlorophenyl)-2-methyl-6-(2-phenylethoxymethyl)-5-(3-phenyl-2-propene-1-ylcarbamoyl)-1,4-dihydro-pyridine-3-carboxylate:

The title compound was obtained from 0.18 g (0.37 mmol) of 3-(2-cyanoethyl) 4-(3-chlorophenyl)-2-methyl-6-(2-phenylethoxymethyl)-1,4-dihydropyridine-3,5-dicarboxylate and 0.06 g (0.45 mmol) of 3-phenyl-2-propene-1-ylamine in the same manner as that of Example 1–4).

Yield: 0.12 g (0.15 mmol) (53.8%) MS (ESI, m/z) 596 (M+H)+1H-NMR (CDCl3): 2.07 (3H, s), 2.66 (2H, t), 2.95 (2H, t), 3.80 (2H, t), 3.95 (2H, m), 4.28 (2H, m), 4.75 (1H, s), 4.75 (1H, d), 4.81 (1H, d), 5.63 (1H, t), 6.05 (1H, dt), 6.24 (1H, dt), 6.77 (1H, s), 7.18–7.34 (14H, m)

2) Synthesis of 4-(3-chlorophenyl)-2-methyl-6-(2-phenylethoxymethyl)-5-(3-phenyl-2-propene-1-ylcarbamoyl)-1,4-dihydropyridine-3-carboxylic acid:

The title compound was obtained from 0.12 g (0.20 mmol) of 2-cyanoethyl 4-(3-chlorophenyl)-2-methyl-6-(2-phenylethoxymethyl)-5-(3-phenyl-2-propene-1-ylcarbamoyl)-1,4-dihydropyridine-3-carboxylate in the same manner as that of Example 1–5).

Yield: 49.3 mg (0.09 mmol) (45.1%) MS (ESI, m/z) 541 (M−H)−1H-NMR (DMSO-d6): 2.22 (3H, s), 2.78 (2H, t), 3.57 (2H, m), 3.77 (2H, m), 4.28 (1H, d), 4.34 (1H, d), 4.91 (1H, s), 6.11 (1H, dt), 6.25 (1H, d), 7.10–7.29 (14H, m), 7.80 (1H, t), 8.24 (1H, s)

EXAMPLE 4

Synthesis of 4-(3-chlorophenyl)-6-(2-cyclohexylethoxymethyl)-2-methyl-5-(3-phenyl-2-propene-1-ylcarbamoyl)-1,4-dihydropyridine-3-carboxylic acid:

1) Synthesis of 2-cyanoethyl 4-(3-chlorophenyl)-6-(2-cyclohexylethoxymethyl)-2-methyl-5-(3-phenyl-2-propene-1-ylcarbamoyl)-1,4-dihydropyridine-3-carboxylate:

The title compound was obtained from 0.31 g (0.64 mmol) of 5-(2-cyanoethyl) 4-(3-chlorophenyl)-2-(2-cyclohexylethoxymethyl)-5-methyl-1,4-dihydropyridine-3,5-dicarboxylate and 0.10 g (0.75 mmol) of 3-phenyl-2-propene-1-ylamine in the same manner as that of Example 1–4).

Yield: 0.13 g (0.22 mmol) (33.9%) MS (ESI, m/z) 602 (M+H)+1H-NMR (CDCl3): 0.85–1.05 (2H, m), 1.15–1.30 (3H, m), 1.38 (1H, m), 1.55 (2H, m), 1.60–1.78 (5H, m), 2.35 (3H, s), 2.68 (2H, t), 3.60 (2H, m), 3.97 (2H, dd), 4.31 (2H, m), 4.75 (2H, s), 4.81 (1H, s), 5.67 (1H, t), 6.07 (1H, dt), 6.25 (1H, dt), 7.18 (1H, s), 7.20–7.34 (9H, m)

2) Synthesis of 4-(3-chlorophenyl)-6-(2-cyclohexylethoxymethyl)-2-methyl-5-(3-phenyl-2-propene-1-ylcarbamoyl)-1,4-dihydropyridine-3-carboxylic acid:

The title compound was obtained from 0.13 g (0.22 mmol) of 2-cyanoethyl 4-(3-chlorophenyl)-6-(2-phenylhexylethoxymethyl)-2-methyl-5-(3-phenyl-2-propene-1-ylcarbamoyl)-1,4-dihydropyridine-3-carboxylate in the same manner as that of Example 1–5).

Yield: 85.2 mg (0.16 mmol) (71.9%) MS (ESI, m/z) 547 (M−H)−1H-NMR (DMSO-d6): 0.68–0.90 (2H, m), 0.98–1.12 (3H, m), 1.21 (1H, m), 1.34 (2H, m), 1.45–1.65 (5H, m), 2.26 (3H, s), 3.36 (2H, t), 3.84 (2H, dd), 4.26 (2H, s), 4.92 (1H, s), 6.16 (1H, dt), 6.30 (1H, d), 7.09–7.30 (9H, m), 7.87 (1H, t), 8.35 (1H, s)

EXAMPLE 5

Synthesis of 4-(3-chlorophenyl)-5-(3,3-diphenylpropylcarbamoyl)-2-methyl-6-(2-(piperidine-1-yl)ethoxy)methyl-1,4-dihydropyridine-3-carboxylic acid 1) Synthesis of benzyl 4-(2-chloroethoxy)acetoacetate:

The title compound was synthesized by a well-known technique (EP 0902016) as follows: 4.0 g (21 mmol) of benzyl acetoacetate was dissolved in 40 ml of ether. 1.1 ml (21 mmol)) of bromine was added dropwise to the obtained solution at 0° C. After stirring at 0° C. for 30 minutes and then at room temperature for 5 hours, about 4 g of ice and sodium carbonate were added until pH of the reaction mixture was increased to 7 or higher. After the extraction with ether, the obtained organic layer was washed with water and saturated aqueous sodium chloride solution, dried over anhydrous magnesium sulfate, concentrated and dried in vacuum to obtain benzyl 4-bromoacetoacetate. 1.68 g (24 mmol) of sodium hydride (60% oily) was suspended in 20 ml of THF. 11.7 g (21 mmol) of 2-chloroethanol was added to the obtained suspension at −40° C. Benzyl 4-bromoacetoacetate obtained as described above was added dropwise thereto at −40° C., then the temperature was slowly elevated to room temperature and they were stirred at that temperature for 16 hours. 1 N hydrochloric acid was added to the reaction mixture. After the extraction with ethyl acetate, the extract was washed with water and saturated aqueous sodium chloride solution, dried over anhydrous magnesium sulfate and concentrated under reduced pressure. The residue was purified by the silica gel chromatography (hexane/ethyl acetate=7/3) to obtain the title compound.

Yield: 3.75 g (14 mmol) (66.6%) 1H-NMR (CDCl3): 3.59 (2H, t), 3.59 (2H, s), 3.72 (2H, t), 4.18 (2H, s), 5.18 (2H, s), 7.35–7.38 (5H, m)

2) Synthesis of 3-benzyl 5-(2-cyanoethyl) 2-(2-chloroethoxy)methyl-4-(3-chlorophenyl)-6-methyl-1,4-dihydropyridine-3,5-dicarboxylate:

0.50 g (1.9 mmol) of benzyl 4-(2-chloroethoxy) acetoacetate, 0.26 g (1.9 mmol) of 3-chlorobenzaldehyde, acetic acid and piperidine were stirred in 3 ml of 2-propanol under heating at room temperature for 24 hours. 0.28 g (1.9 mmol) of 2-cyanoethyl 3-aminocrotonate was added to the obtained mixture, and they were stirred under heating at 50° C. for 48 hours. 2-Propanol was evaporated under reduced pressure, and the residue was purified by the silica gel chromatography (hexane/ethyl acetate=1/1) to obtain the title compound.

Yield: 0.34 g (0.64 mmol) (34.8%) MS (ESI, m/z)531 (M+H)+1H-NMR (CDCl3): 2.39 (3H, s), 2.59 (2H, t), 3.73

(2H, t), 3.79 (2H, m), 4.22 (2H, m), 4.75 (1H, d), 4.82 (1H, d), 4.98 (1H, s), 5.00 (1H, d), 5.13 (1H, d), 7.11–7.30 (10H, m)

3) Synthesis of 5-(2-cyanoethyl) 2-(2-chloroethoxy)methyl-4-(3-chlorophenyl)-6-methyl-1,4-dihydropyridine-3,5-dicarboxylate:

The title compound was obtained from 0.34 g (0.64 mmol) of 3-benzyl 5-(2-cyanoethyl) 2-(2-chloroethoxy)methyl-4-(3-chlorophenyl)-6-methyl-1,4-dihydropyridine-3,5-dicarboxylate in the same manner as that of Example 1–3).

Yield: 0.25 g (0.56 mmol) (86.8%) MS (ESI, m/z) 437 (M−H)−1H-NMR (CDCl3): 2.41 (3H, s), 2.63 (2H, t), 3.74 (2H, m), 3.86 (2H, m), 4.25 (2H, m), 4.75 (1H, d), 4.81 (1H, d), 4.95 (1H, s), 7.13–7.26 (4H, m), 7.47 (1H, s)

4) Synthesis of (2-cyanoethyl) 6-(2-chloroethoxy)methyl-4-(3-chlorophenyl)-5-(3,3- diphenylpropylcarbamoyl)-2-methyl-1,4-dihydropyridine-3-carboxylate:

The title compound was obtained from 0.25 g (0.56 mmol) of 5-(2-cyanoethyl) 2-(2-chloroethoxy)methyl-4-(3-chlorophenyl)-6-methyl-1,4-dihydropyridine-3,5-dicarboxylate in the same manner as that of Example 1–4).

Yield: 0.28 g (0.45 mmol) (80.2%) MS (ESI, m/z) 632 (M+H)+1H-NMR (CDCl3): 2.14 (2H, s), 2.67 (2H, t), 3.10 (2H, m), 3.72 (2H, m), 3.83 (2H, m), 4.31 (2H, m), 4.73 (1H, s), 4.82 (2H, s), 5.56 (1H, t), 7.11–7.26 (15H, m)

5) Synthesis of (2-cyanoethyl) 4-(3-chlorophenyl)-5-(3,3-diphenyl-propylcarbamoyl)-2-methyl-6-(2-(piperidine-1-yl)ethoxy)methyl-1,4-dihydropyridine-3-carboxylate:

0.22 g (0.34 mmol) of (2-cyanoethyl) 6-(2-chloroethoxy)methyl-4-(3-chlorophenyl-5-(3,3-diphenylpropylcarbamoyl)-2-methyl-1,4-dihydropyridine-3-carboxylate was dissolved in 3 ml of 2-propanol. 0.50 g (0.33 mmol) of sodium iodide was added to the obtained solution, and they were stirred at 60° C. for 70 hours. The solution was left to stand at 5° C. overnight, and sodium iodide thus precipitated was separated by the filtration. The filtrate was removed under reduced pressure and the product was stirred together with 35 mg (0.43 mmol) of piperidine in 9 ml of acetonitrile at 50° C. for 18 hours. Ethyl acetate was added to the reaction mixture. After washing the product with water and saturated aqueous sodium chloride solution, the organic layer was dried over anhydrous magnesium sulfate and concentrated under reduced pressure. The residue was purified by the silica gel chromatography (chloroform/methanol=9/1) to obtain the title compound.

Yield: 0.10 g (0.15 mmol) (50.8%) MS (ESI, m/z) 681 (M+H)+1H-NMR (CDCl3): 1.40–1.50 (2H, m), 1.56–1.66 (3H, m), 2.15 (2H, q), 2.37 (3H, s), 2.40–2.53 (5H, m), 2.59 (2H, m), 2.67 (2H, t), 3.10 (2H, q), 3.69 (1H, t), 3.66 (2H, t), 4.30 (2H, m), 4.72 (3H, s), 5.54 (1H, t), 7.09–7.30 (14H, m), 7.83 (1H, s)

6) Synthesis of 4-(3-chlorophenyl)-5-(3,3-diphenylpropylcarbamoyl)-2-methyl-6-(2-(piperidine-1-yl)ethoxy)methyl-1,4-dihydropyridine-3-carboxylic acid:

The title compound was obtained from 0.10 g (0.15 mmol) of (2-cyanoethyl) 4-(3-chlorophenyl)-5-(3,3-diphenylpropylcarbamoyl)-2-methyl-6-(2-(piperidine-1-yl)ethoxy)methyl-1,4-dihydropyridine-3-carboxylate in the same manner as that of Example 1–5).

Yield: 36 mg (0.06 mmol) (37.4%) MS (ESI, m/z) 626 (M−H)−1H-NMR (DMSO-d6): 1.20–1.45 (5H, m), 2.10 (2H, q), 2.26 (3H, s), 2.26–2.44 (5H, m), 2.42 (2H, m), 2.94 (2H, m), 3.44 (2H, m), 3.84 (1H, t), 4.26 (2H, s), 4.89 (1H, s), 7.07–7.26 (14H, m), 7.74 (1H, t), 8.32 (1H, s)

EXAMPLE 6

Synthesis of 4-(3-chlorophenyl)-5-(3,3-diphenylpropylcarbamoyl)-2-methyl-6-(2-(pyridine-2-yl)ethoxy)methyl-1,4-dihydropyridine-3-carboxylic acid:

1) Synthesis of benzyl 4-(2-pyridine-2-yl)ethoxy) acetoacetate:

0.71 g (17.8 mmol) of sodium hydride (60% oily) was suspended in 6 ml of THF. 1.30 g (10.6 mmol) of 2-(2-pyridine)ethanol was added to the obtained suspension at 0° C. and they were stirred at room temperature for 30 minutes. 2.00 g (8.82 mmol) of benzyl 4-chloroacetoacetate was added to the obtained mixture at room temperature and they were stirred also at room temperature for 16 hours. 0.1 N hydrochloric acid was added to the reaction mixture. After the extraction with ethyl acetate, the organic layer was washed successively with 1 N aqueous sodium hydroxide solution, water and saturated aqueous sodium chloride solution. The product was dried over anhydrous magnesium sulfate and then concentrated under reduced pressure. The residue was purified by the silica gel chromatography (hexane/ethyl acetate=1/9) to obtain the title compound.

Yield: 1.08 g (3.45 mmol) (39.1%) MS (ESI, m/z) 314 (M+H)+1H-NMR (CDCl3): 3.05 (2H, t), 3.50 (2H, s), 3.86 (2H, t), 4.08 (2H, s), 5.14 (2H, s), 7.10–7.20 (2H, m), 7.30–7.40 (5H, m), 7.59 (1H, td), 8.54 (1H, dd)

2) Synthesis of 5-benzyl 3-(2-cyanoethyl) 4-(3-chlorophenyl)-2-methyl-6-(2-(pyridine-2-yl)ethoxy)methyl-1,4-dihydropyridine-3,5-dicarboxylate:

The title compound was obtained from 0.50 g (1.60 mmol) of benzyl 4-(2-(pyridine-2-yl)ethoxy)acetoacetate and 0.23 g (1.63 mmol) of 3-chlorobenzaldehyde in the same manner as that of Example 5–2).

Yield: 0.51 g (0.089 mmol) (55.7%) MS (ESI, m/z) 572 (M+H)+1H-NMR (CDCl3): 2.29 (3H, s), 2.66 (2H, t), 3.14 (2H, t), 3.97 (2H, t), 4.25 (2H, m), 4.74 (2H, s), 4.95 (1H, s), 5.00 (1H, d), 5.12 (1H, d), 7.16–7.34 (11H, m), 7.42 (1H, s), 7.63 (1H, td), 8.60 (1H, dd)

3) Synthesis of 3-(2-cyanoethyl) 4-(3-chlorophenyl)-2-methyl-6-(2-(pyridine-2-yl)ethoxy)methyl-1,4-dihydropyridine-3,5-dicarboxylate:

The title compound was obtained from 0.15 g (0.26 mmol) of 5-benzyl 3-(2-cyanoethyl) 4-(3-chlorophenyl)-2-methyl-6-(2-(pyridine-2-yl)ethoxy) methyl-1,4-dihydropyridine-3,5-dicarboxylate in the same manner as that of Example 1–3).

Yield: 0.083 g (0.17 mmol) (65.4%) 1H-NMR (CDCl3): 2.25 (3H, s), 2.59 (2H, t), 3.12 (2H, t), 3.94 (2H, t), 4.22 (2H, m), 4.64 (1H, d), 4.72 (1H, d), 4.95 (1H, s), 7.08–7.35 (6H, m), 7.40 (1H, s), 7.64 (1H, td), 8.59 (1H, dd)

4) Synthesis of (2-cyanoethyl) 4-(3-chlorophenyl)-5-(3,3-diphenylpropylcarbamoyl)-2-methyl-6-(2-(pyridine-2-yl)ethoxy)methyl-1,4-dihydropyridine-3-carboxylate:

The title compound was obtained from 0.083 g (0.17 mmol) of 3-(2-cyanoethyl) 4-(3-chlorophenyl)-2-methyl-6-(2-(pyridine-2-yl)ethoxy)methyl-1,4-dihydropyridine-3,5-dicarboxylate in the same manner as that of Example 1–4).

Yield: 0.10 g (0.15 mmol) (90.6%) MS (ESI, m/z) 675 (M+H)+1H-NMR (CDCl3): 2.15 (2H, m), 2.23 (3H, s), 2.67 (2H,t), 3.10 (2H, m), 3.13 (2H, t), 3.68 (1H, t), 3.97 (2H, m), 4.31 (2H, m), 4.70 (1H, d), 4.74 (1H, s), 4.78 (1H, d), 5.48 (1H, t), 7.11–7.30 (17H, m), 7.63 (1H, td), 8.59 (1H, dd)

5) Synthesis of 4-(3-chlorophenyl)-5-(3,3-diphenylpropylcarbamoyl)-2-methyl-6-(2-(pyridine-2-yl)ethoxy)methyl-1,4-dihydropyridine-3-carboxylic acid:

The title compound was obtained from 0.10 g (0.15 mmol) of (2-cyanoethyl) 4-(3-chlorophenyl)-5-(3,3- diphenylpropylcarbamoyl)-2-methyl-6-(2-(pyridine-2-yl) ethoxy)methyl-1,4-dihydropyridine-3-carboxylate in the same manner as that of Example 1–5).

Yield: 72 mg (0.13 mmol) (88.5%) MS (ESI, m/z) 620 (M−H)−1H-NMR (DMSO-d6): 2.05 (2H, q), 2.22 (3H, s), 2.90 (2H, m), 2.95 (2H, t), 3.72 (2H, m), 3.80 (1H, t), 4.22 (1H, d), 4.34 (1H, d), 4.86 (1H, s), 7.07–7.26 (16H, m), 7.61 (2H, m), 8.21 (1H, s), 8.40 (1H, d)

EXAMPLE 7

Synthesis of 4-(3-chlorophenyl)-5-(3,3-diphenylpropylcarbamoyl)-6-methyl-2-(2-pyridine-2-yl)ethoxy)methyl-1,4-dihydropyridine-3-carboxylic acid:

1) Synthesis of 5-benzyl 4-(3-chlorophenyl)-2-methyl-6-(2-(pyridine-2-yl)ethoxy)methyl-1,4-dihydropyridine-3,5-dicarboxylate:

0.23 g (0.40 mmol) of the compound obtained in Example 6–2) was dissolved in 5 ml of methanol. 0.50 ml of 1 N aqueous sodium hydroxide solution was added to the obtained solution, and they were stirred at room temperature for 6 hours. 1 N hydrochloric acid and water were added to the reaction mixture. After the extraction with ethyl acetate, the organic layer was concentrated and dried under reduced pressure to obtain the title compound.

Yield: 0.20 g (0.39 mmol) (95.8%) MS (ESI, m/z) 517 (M−H)−1H-NMR (CDCl3): 2.25 (3H, s), 3.13 (2H, t), 3.94 (2H, t), 4.70 (1H, d), 4.75 (1H, d), 4.97 (1H, s), 4.99 (1H, d), 5.12 (1H, s), 5.92 (1H, s), 7.08–7.40 (11H, m), 7.66 (1H, td), 8.59 (1H, dd)

2) Synthesis of benzyl 4-(3-chlorophenyl)-5-(3,3-diphenylpropylcarbamoyl)-6-methyl-2-(2-(pyridine-2-yl)ethoxy)methyl-1,4-dihydropyridine-3-carboxylate:

0.20 g (0.39 mmol) of 5-benzyl 4-(3-chlorophenyl)-2-methyl-6-(2-(pyridine-2-yl)ethoxy)methyl-1,4-dihydropyridine-3,5-dicarboxylate, 0.08 g (0.42 mmol) of WSC hydrochloride and 0.09 g (0.43 mmol) of 3,3-diphenylpropylamine were stirred in 5 ml of dichloromethane at room temperature for 24 hours. Dichloromethane was evaporated under reduced pressure, and water was added to the residue. After the extraction with ethyl acetate, the organic layer was dried over anhydrous magnesium sulfate and then concentrated under reduced pressure. The residue was purified by the silica gel chromatography (hexane/ethyl acetate=4/6) to obtain the title compound.

Yield: 0.15 g (0.21 mmol) (54.6%) MS (ESI, m/z) 712 (M+H)+1H-NMR (CDCl3): 2.10 (2H, m), 2.12 (3H, s), 3.10 (2H, m), 3.11 (2H, t), 3.65 (1H, t), 3.94 (2H, t), 4.65 (1H, d), 4.72 (1H, s), 4.75 (1H, d), 5.00 (1H, d), 5.14 (1H, d), 5.22 (1H, t), 7.07–7.37 (22H, m), 7.63 (1H, td), 8.58 (1H, dd)

3) Synthesis of 4-(3-chlorophenyl)-5-(3,3-diphenylpropylcarbamoyl)-6-methyl-2-(2-pyridine-2-yl)ethoxy)methyl-1,4-dihydropyridine-3-carboxylic acid:

The title compound was obtained from 0.15 g (0.24 mmol) of benzyl 4-(3-chlorophenyl)-5-(3,3-diphenylpropylcarbamoyl)-6-methyl-2-(2-(pyridine-2-yl)ethoxy)methyl-1,4-dihydropyridine-3-carboxylate in the same manner as that of Example 1–3).

Yield: 13.6 mg (0.02 mmol) (9.1%) MS (ESI, m/z) 620 (M−H)−1H-NMR (CDCl3): 2.10 (2H, m), 2.17 (3H, s), 3.10 (2H, m), 3.12 (2H, t), 3.65 (1H, t), 3.94 (2H, t), 4.62 (1H, d), 4.68 (1H, d), 4.69 (1H, s), 5.32 (1H, t), 7.05–7.40 (17H, m), 7.62 (1H, td), 8.59 (1H, d)

EXAMPLE 8

Synthesis of methyl 6-(2-aminoethoxy)methyl-4-(3-chlorophenyl)-5-(3,3-diphenylpropylcarbamoyl)-2-methyl-1,4-dihydropyridine-3-carboxylate:

1) Synthesis of 3-benzyl 5-methyl 2-(2-chloroethoxy) methyl-4-(3-chlorophenyl)-6-methyl-1,4-dihydropyridine-3,5-dicarboxylate:

1.2 g (4.5 mmol) of benzyl 4-(2-chloroethoxy) acetoacetate, 0.75 g (5.3 mmol) of 3-chlorobenzaldehyde, acetic-acid and piperidine were stirred together in 3 ml of 2-propanol at room temperature for 24 hours. The solvent was evaporated under reduced pressure and the product was purified by the silica gel chromatography (hexane/ethyl acetate=5/1). 0.27 g (2.3 mmol) of methyl 3-aminocrotonate was added to the obtained compound, and they were stirred under heating at 60° C. for 20 hours. 2-Propanol was evaporated under reduced pressure, and the residue was purified by the silica gel chromatography (hexane/ethyl acetate=1/1) to obtain the title compound.

Yield: 0.41 g (0.84 mmol) (48.6%) MS (ESI, m/z) 490 (M+H)+1H-NMR (CDCl3): 2.37 (3H, s), 3.63 (3H, s), 3.73 (2H, m), 3.81 (2H, m), 4.78 (1H, d), 4.82 (1H, d), 4.99 (1H, s), 5.00 (1H, d), 5.12 (1H, d), 7.11–7.38 (10H, m)

2) Synthesis of 5-methyl 2-(2-chloroethoxy)methyl-4-(3-chlorophenyl)-6-methyl-1,4-dihydropyridine-3,5-dicarboxylate The title compound was obtained from 0.41 g (0.84 mmol) of 3-benzyl 5-methyl 2-(2-chloroethoxy)methyl-4-(3-chlorophenyl)-6-methyl-1,4-dihydropyridine-3,5-dicarboxylate in the same manner as that of Example 1–3).

Yield: 0.26 g (0.65 mmol) (77.3%) MS (ESI, m/z) 398 (M−H)−1H-NMR (CDCl3): 2.40 (3H, s), 3.65 (3H, s), 3.72 (2H, m), 3.82 (2H, m), 4.72 (1H, d), 4.80 (1H, d), 4.98 (1H, s), 7.10–7.30 (4H, m), 7.39 (1H, s)

3) Synthesis of methyl 6-(2-chloroethoxy)methyl-4-(3-chlorophenyl)-5-(3,3-diphenylpropylcarbamoyl)-2-methyl-1,4-dihydropyridine-3-carboxylate:

The title compound was obtained from 0.079 g (0.20 mmol) of 5-methyl 2-(2-chloroethoxy)methyl-4-(3-chlorophenyl)-6-methyl-1,4-dihydropyridine-3,5-dicarboxylate in the same manner as that of Example 7–2).

Yield: (quantitative yield) MS (ESI, m/z) 593 (M+H)+ 1H-NMR (CDCl3): 2.15 (2H, m), 2.31 (3H, s), 3.10 (2H, m), 3.68 (1H, t), 3.69 (3H, s), 3.73 (2H, m), 3.82 (2H, m), 4.73 (1H, d), 5.48 (1H, t), 4.86 (2H, s), 7.08–7.40 (15H, m)

4) Synthesis of methyl 6-(2-azidoethoxy)methyl-4-(3-chlorophenyl)-5-(3,3-diphenylpropylcarbamoyl)-2-methyl-1,4-dihydropyridine-3-carboxylate:

0.12 g (0.20 mmol) of methyl 6-(2-chloroethoxy)methyl-4-(3-chlorophenyl)-5-(3,3-diphenylpropylcarbamoyl)-2-methyl-1,4-dihydropyridine-3-carboxylate and 0.030 g (0.20 mmol) of sodium iodide were dissolved in 2 ml of 2-propanol, and the obtained solution was stirred at 70° C. for 24 hours. The solvent was evaporated under reduced pressure. Dichloromethane was added to the residue, and sodium iodide thus precipitated was separated by the filtration. The filtrate was treated under reduced pressure, and 15 mg (0.23 mmol) of sodium azide and 2 ml of DMF were added thereto. The reaction mixture was stirred at 50° C. for 16 hours. Ethyl acetate was added thereto. After washing with water and saturated aqueous sodium chloride solution, the organic layer was concentrated under reduced pressure. The residue was purified by the silica gel chromatography (hexane/ethyl acetate=7/3) to obtain the title compound.

Yield: 0.087 g (0.15 mmol) (72.5%) MS (ESI, m/z) 600 (M+H)+1H-NMR (CDCl3): 2.15 (2H, m), 2.31 (3H, s), 3.11 (2H, m), 3.48 (2H, m), 3.66 (1H, t), 3.71 (3H, s), 3.76 (2H, m), 4.73 (1H, s), 4.83 (1H, d), 4.90 (1H, d), 5.49 (1H, t), 7.02 (1H, s), 7.09–7.38 (14H, m)

5) Synthesis of methyl 6-(2-aminoethoxy)methyl-4-(3-chlorophenyl)-5-(3,3-diphenylpropylcarbamoyl)-2-methyl-1,4-dihydropyridine-3-carboxylate:

The title compound was obtained from 0.087 g (0.15 mmol) of methyl 6-(2-azidoethoxy)methyl-4-(3-chlorophenyl)-5-(3,3-diphenylpropylcarbamoyl)-2-methyl-1,4-dihydropyridine-3-carboxylate in the same manner as that of Example 1–3).

Yield: 50 mg (0.087 mmol) (58.1%) MS (ESI, m/z) 574 (M–H)–1H-NMR (CDCl3): 2.16 (2H, m), 2.31 (3H, s), 2.96 (2H, t), 3.09 (2H, m), 3.60 (2H, m), 3.66 (1H, t), 3.69 (3H, s), 4.73 (1H, s), 4.78 (2H, s), 5.50 (1H, t), 7.05–7.35 (14H, m), 7.72 (1H, s)

EXAMPLE 9

Synthesis of methyl 6-(2-aminoethoxy)methyl-4-(3-chlorophenyl)-2-methyl-5-(3-(N-morpholino)propylcarbamoyl)-1,4-dihydropyridine-3-carboxylate:

1) Synthesis of methyl 6-(2-chloroethoxy)methyl-4-(3-chlorophenyl)-2-methyl-5-(3-(N-morpholino)propylcarbamoyl)-1,4-dihydropyridine-3-carboxylate:

0.079 g (0.20 mmol) of the compound obtained in Example 8–2), 0.045 g (0.23 mmol) of WSC hydrochloride and 0.035 g (0.24 mmol) of N-(3-aminopropyl)morpholine were stirred together in 2 ml of dichloromethane at room temperature for 20 hours. The solvent was evaporated under reduced pressure, and the residue was suspended in ethyl acetate and then washed with water and saturated aqueous sodium chloride solution. After drying over anhydrous magnesium sulfate, the solvent was evaporated and the residue was dried under reduced pressure to obtain the title compound.

Yield: (quantitative yield) MS (ESI, m/z) 526 (M+H)+ 1H-NMR (CDCl3): 1.61 (2H, m), 2.23 (2H, t), 2.26–2.40 (7H, m), 3.22 (2H, m), 3.65–3.72 (7H, m), 3.73 (2H, m), 3.81 (2H, m), 4.79 (1H, s), 4.85 (2H, s), 6.20 (1H, t), 7.15–7.35 (5H, m)

2) Synthesis of methyl 6-(2-azidoethoxy)methyl-4-(3-chlorophenyl)-2-methyl-5-(3-(N-morpholino)propylcarbamoyl)-1,4-dihydropyridine-3-carboxylate:

The title compound was obtained from 0.11 g (0.20 mmol) of methyl 6-(2-chloroethoxy)methyl-4-(3-chlorophenyl)-2-methyl-5-(3-(N-morpholino)propylcarbamoyl)-1,4-dihydropyridine-3-carboxylate in the same manner as that of Example 8–4).

Yield: 0.080 g (0.15 mmol) (74.9%) MS (ESI, m/z) 533 (M+H)+1H-NMR (CDCl3): 1.56 (2H, m), 2.21 (2H, t), 2.25–2.35 (7H, m), 3.22 (2H, m), 3.45 (2H, m), 3.65 (7H, m), 3.71 (2H, m), 4.76 (1H, d), 4.77 (1H, s), 4.82 (1H, d), 6.12 (1H, t), 7.00 (1H, s), 7.13–7.35 (4H, m)

3) Synthesis of methyl 6-(2-aminoethoxy)methyl-4-(3-chlorophenyl)-2-methyl-5-(3-(N-morpholino)propylcarbamoyl)-1,4-dihydropyridine-3-carboxylate 2 ml of ethyl acetate and 10% palladium/carbon were added to 0.080 g (0.15 mmol) of methyl 6-(2-azidoethoxy)methyl-4-(3-chlorophenyl)-2-methyl-5-(3-(N-morpholino)propylcarbamoyl)-1,4-dihydropyridine-3-carboxylate, and they were stirred at room temperature in hydrogen atmosphere under normal pressure for 24 hours. The reaction mixture was filtered, and the filtrate was evaporated under reduced pressure. The residue was purified by the basic silica gel column chromatography (chloroform/methanol=97/3) to obtain the title compound.

Yield: 60 mg (0.12 mmol) (78.4%) MS (ESI, m/z) 507 M–H)–1H-NMR (CDCl3): 1.58 (2H, m), 2.23 (2H, t), 2.28–2.38 (7H, m), 2.95 (2H, t), 3.23 (2H, m), 3.58 (2H, t), 3.66 (7H, m), 4.76 (2H, s), 4.78 (1H, s), 6.18 (1H, t), 7.10–7.30 (4H, m), 7.66 (1H, s)

EXAMPLE 10

Synthesis of 6-(2-aminoethoxy)methyl-4-(3-chlorophenyl)-5-(3,3-diphenylpropylcarbamoyl)-2-methoxymethyl-1,4-dihydropyridine-3-carboxylic acid:

1) Synthesis of 3-benzyl 5-(2-cyanoethyl) 2-(2-chloroethoxy)methyl-4-(3-chlorophenyl)-6-methoxymethyl-1,4-dihyropyridine-3,5-dicarboxylate:

The title compound was obtained from 0.20 g (0.74 mmol) of benzyl 4-(2-chloroethoxy)acetoacetate, 0.088 g (0.63 mmol) of 3-chlorobenzaldehyde and 0.12 g (0.78 mmol) of (2-cyanoethyl) 3-amino-4-methoxymethylcrotonate in the same manner as that of Example 1–3).

Yield: 0.18 g (0.33 mmol) (44.0%) MS (ESI, m/z) 559 (M+H)+1H-NMR (CDCl3): 2.59 (2H, t), 3.49 (3H, s), 3.70 (2H, t), 3.82 (2H, m), 4.23 (2H, m), 4.62 (1H, d), 4.72 (1H, d), 4.79 (1H, d), 4.85 (1H, d), 4.98 (1H, s), 5.00 (1H, d), 5.12 (1H, d), 7.11–7.38 (9H, m), 8.63 (1H, s)

2) Synthesis of 5-(2-cyanoethyl) 2-(2-chloroethoxy)methyl-4-(3-chlorophenyl)-6-methoxymethyl-1,4-dihydropyridine-3,5-dicarboxylate:

The title compound was obtained from 0.18 g (0.033 mmol) of 3-benzyl 5-(2-cyanoethyl) 2-(2-chloroethoxy)methyl-4-(3-chlorophenyl)-6-methoxy-methyl-1,4-dihydropyridine-3,5-dicarboxylate in the same manner as that of Example 1–3).

Yield: (quantitative yield) MS (ESI, m/z) 467 (M–H)–1H-NMR (CDCl3): 2.60 (2H, m), 3.49 (3H, s), 3.69 (2H, m), 3.75 (2H, m), 4.20 (2H, m), 4.60 (1H, d), 4.68 (1H, d), 4.70 (1H, d), 4.80 (1H, d), 4.98 (1H, s), 7.05–7.35 (4H, m), 8.55 (1H, s)

3) Synthesis of (2-cyanoethyl) 6-(2-chloroethoxy)methyl-4-(3-chlorophenyl)-5-(3,3-diphenylpropylcarbamoyl)-2-methoxymethyl-1,4-dihydropyridine-3-carboxylate:

The title compound was obtained from 0.16 g (0.33 mmol) of 5-(2-cyanoethyl) 2-(2-chloroethoxy)methyl-4-(3-chlorophenyl)-6-methoxymethyl-1,4-dihydropyridine-3,5-dicarboxylate in the same manner as that of Example 7–2).

Yield: 0.16 g (0.24 mmol) (72.2%) MS (ESI, m/z) 662 (M+H)+1H-NMR (CDCl3): 2.15 (2H, m), 2.67 (2H, t), 3.10 (2H, m), 3.47 (3H, s), 3.68 (1H, t), 3.70 (2H, t), 3.81 (2H, m), 4.29 (2H, m), 4.52 (1H, d), 4.62 (1H, d), 4.74 (1H, s), 4.81 (2H, s), 5.58 (1H, t), 7.10–7.35 (14H, m), 8.42 (1H, s)

4) Synthesis of (2-cyanoethyl) 6-(2-azidoethoxy)methyl-4-(3-chlorophenyl)-5-(3,3-diphenylpropylcarbamoyl)-2-methoxymethyl-1,4-dihydropyridine-3-carboxylate:

The title compound was obtained from 0.16 g (0.24 mmol) of (2-cyanoethyl) 6-(2-chloroethoxy)methyl-4-(3-chlorophenyl)-5-(3,3-diphenyl-propylcarbamoyl)-2-methoxymethyl-1,4-dihydropyridine-3-carboxylate in the same manner as that of Example 8–4).

Yield: 0.14 g (0.21 mmol) (87.2%) MS (ESI, m/z) 669 (M+H)+1H-NMR (CDCl3) 2.15 (2H, m), 2.68 (2H, t), 3.10 (2H, m), 3.48 (5H, m), 3.68 (1H, t), 3.71 (2H, m), 4.32 (2H, m), 4.56 (1H, d), 4.66 (1H, d), 4.74 (1H, s), 4.81 (2H, s), 5.52 (1H, t), 7.10–7.35 (14H, m), 8.33 (1H, s)

5) Synthesis of (2-cyanoethyl) 6-(2-aminoethoxy)methyl-4-(3-chlorophenyl)-5-(3,3-diphenylpropylcarbamoyl)-2-methoxymethyl-1,4-dihydropyridine-3-carboxylate:

The title compound was obtained from 0.14 g (0.21 mmol) of (2-cyanoethyl) 6-(2-azidoethoxy)methyl-4-(3-chlorophenyl)-5-(3,3-diphenylpropylcarbamoyl)-2- methoxymethyl-1,4-dihydropyridine-3-carboxylate in the same manner as that of Example 9–3).

Yield: 65 mg (0.10 mmol) (47.6%) MS (ESI, m/z) 643 (M+H)+1H-NMR (CDCl3): 2.15 (2H, m), 2.66 (2H, t), 2.93 (2H, m), 3.12 (2H, m), 3.47 (3H, s), 3.58 (2H, m), 3.68 (1H, t), 4.29 (2H, m), 4.52 (1H, d), 4.68 (1H, d), 4.75 (1H, s), 4.76 (2H, s), 5.58 (1H, t), 7.10–7.30 (14H, m), 8.40 (1H, s)

6) Synthesis of 6-(2-aminoethoxy)methyl-4-(3-chlorophenyl)-5-(3,3-diphenylpropylcarbamoyl)-2-methoxymethyl-1,4-dihydropyridine-3-carboxylic acid:

0.065 g (0.10 mmol) of (2-cyanoethyl) 6-(2-aminoethoxy) methyl-4-(3-chlorophenyl)-5-(3,3-diphenylpropylcarbamoyl)-2-methoxymethyl-1,4-dihydropyridine-3-carboxylate was dissolved in 1 ml of methanol. 0.20 ml of 1 N aqueous sodium hydroxide solution was added to the obtained solution, and they were stirred at room temperature for 8 hours. The reaction mixture was neutralized with 1 N hydrochloric acid. After the extraction with ethyl acetate, the solvent was evaporated and the product was purified by TLC (Silanised Silica gel, methanol/water=6/4) to obtain the title compound.

Yield: 16 mg (0.027 mmol) (26.6%) MS (ESI, m/z) 489 (M–H)–1H-NMR (CD3OD): 2.10 (2H, m), 2.82 (2H, m), 3.00 (2H, m), 3.36 (3H, s), 3.51 (2H, m), 3.68 (1H, t), 4.44 (1H, d), 4.60 (1H, d), 4.66 (1H, d), 4.72 (1H, d), 5.14 (1H, s), 7.05–7.35 (16H, m)

EXAMPLE 11

Synthesis of Methyl 6-(2-aminoethoxy)methyl-4-(3-chlorophenyl)-5-(3,3-diphenylpropylcarbamoyl)-2-methoxymethyl-1,4-dihydropyridine-3-carboxylate:

1) Synthesis of 3-benzyl 5-methyl 2-(2-chloroethoxy) methyl-4-(3-chlorophenyl)-6-methoxymethyl-1,4-dihydropyridine-3,5-dicarboxylate:

0.35 g (0.89 mmol) of benzyl 2-(2-chloroethoxy)acetyl-3-(3-chlorophenyl)acrylate and 0.10 g (0.69 mmol) of methyl 3-amino-4-methoxycrotonate were stirred in 2 ml of 2-propanol at 70° C. for 24 hours. The solvent was evaporated under reduced pressure, and the residue was purified by the silica gel chromatography (hexane/ethyl acetate=7/3) to obtain the title compound.

Yield: 0.20 g (0.38 mmol) (55.1%) MS (ESI, m/z) 520 (M+H)+1H-NMR (CDCl3): 3.47 (3H, s), 3.62 (3H, s), 3.70 (2H, m), 3.81 (2H, m), 4.5–5.2 (7H, m), 7.11–7.40 (10H, m)

2) Synthesis of 5-methyl 2-(2-chloroethoxy)methyl-4-(3-chlorophenyl)-6-methoxymethyl-1,4-dihydropyridine-3,5-dicarboxylate:

The title compound was obtained from 0.20 g (0.38 mmol) of 3-benzyl 5-methyl 2-(2-chloroethoxy)methyl-4-(3-chlorophenyl)-6-methoxymethyl-1,4-dihydropyridine-3,5-dicarboxylate in the same manner as that of Example 1–3).

Yield: (quantitative yield) MS (ESI, m/z) 428 (M–H)–1H-NMR (CDCl3): 3.49 (3H, s), 3.66 (3H, s), 3.73 (2H, m), 3.85 (2H, m), 4.72 (3H, s), 4.75 (1H, d), 4.83 (1H, d), 7.10–7.25 (4H, m), 8.62 (1H, s)

3) Synthesis of methyl 6-(2-chloroethoxy)methyl-4-(3-chlorophenyl)-5-(3,3-diphenylpropylcarbamoyl)-2-methoxymethyl-1,4-dihydropyridine-3-carboxylate:

The title compound was obtained from 0.084 g (0.20 mmol) of 5-methyl 2-(2-chloroethoxy)methyl-4-(3-chlorophenyl)-6-methoxymethyl-1,4-dihydropyridine-3,5-dicarboxylate in the same manner as that of Example 7–2).

Yield: 0.054 g (0.087 mmol) (44.4%) MS (ESI, m/z) 623 (M+H)+1H-NMR (CDCl3): 2.15 (2H, m), 3.10 (2H, m), 3.45 (3H, s), 3.62–3.72 (6H, m), 3.83 (2H, m), 4.55 (1H, d), 4.65 (1H, d), 4.72 (1H, s), 4.83 (2H, s), 5.48 (1H, t), 7.08–7.30 (14H, m), 8.35 (1H, s)

4) Synthesis of Methyl 6-(2-azidoethoxy)methyl-4-(3-chlorophenyl)-5-(3,3-diphenylpropylcarbamoyl)-2-methoxymethyl-1,4-dihydropyridine-3-carboxylate:

0.54 g (0.087 mmol) of methyl 6-(2-chloroethoxy) methyl-4-(3-chlorophenyl)-5-(3,3-diphenylpropylcarbamoyl)-2-methoxymethyl-1,4-dihydropyridine-3-carboxylate, 10 mg (0.15 mmol) of sodium azide and 2.0 mg (0.013 mmol) of sodium iodide were dissolved in 2 ml of DMF, and the obtained solution was stirred at 60° C. for 44 hours. Ethyl acetate was added to the solution. After washing with water and saturated aqueous sodium chloride solution, the organic layer was concentrated under reduced pressure. The residue was purified by the silica gel chromatography (hexane/ethyl acetate= 1/1) to obtain the title compound.

Yield: 0.040 g (0.063 mmol) (73.3%) MS (ESI, m/z) 630 (M+H)+1H-NMR (CDCl3): 2.15 (2H, m), 3.10 (2H, m), 3.46 (3H, s), 3.48 (2H, m), 3.64 (1H, t), 3.70 (3H, s), 3.74 (2H, m), 4.53 (1H, d), 4.64 (1H, d), 4.72 (1H, s), 4.84 (2H, s), 5.48 (1H, t), 7.08–7.38 (14H, m), 8.25 (1H, s)

5) Synthesis of Methyl 6-(2-aminoethoxy)methyl-4-(3-chlorophenyl)-5-(3,3-diphenylpropylcarbamoyl)-2-methoxymethyl-1,4-dihydropyridine-3-carboxylate:

The title compound was obtained from 0.040 g (0.063 mmol) of methyl 6-(2-acidoethoxy)methyl-4-(3-chlorophenyl)-5-(3,3-diphenylpropylcarbamoyl)-2-methoxymethyl-1,4-dihydropyridine-3-carboxylate in the same manner as that of Example 9–3).

Yield: 29 mg (0.048 mmol) (75.4%) MS (ESI, m/z) 602 (M–H)–1H-NMR (CDCl3): 2.15 (2H, m), 2.93 (2H, t), 3.10 (2H, m), 3.45 (3H, s), 3.58 (2H, m), 3.66 (1H, t), 3.70 (3H, s), 4.50 (1H, d), 4.70 (1H, d), 4.74 (1H, s), 4.80 (2H, s), 5.52 (1H, t), 7.08–7.38 (14H, m), 8.30 (1H, s)

EXAMPLE 12

Synthesis of 2-(2-aminoethoxy)methyl-4-(3-chlorophenyl)-5-cyano-3-(3,3-diphenylpropylcarbamoyl)-6-methyl-1,4-dihydropyridine:

1) Synthesis of Benzyl 2-(2-chloroethoxy)methyl-4-(3-chlorophenyl)-5-cyano-6-methyl-1,4-dihydropyridine-3-carboxylate:

The title compound was obtained from 1.0 g (3.7 mmol) of benzyl 4-(2-chloroethoxy)methylacetoacetate, 0.52 g (3.7 mmol) of 3-chlorobenzaldehyde and 0.30 g (3.7 mmol) of 3-aminocrotonitrile in the same manner as that of Example 1–2).

Yield: 0.84 g (1.8 mmol) (49.9%) MS (ESI, m/z) 457 (M+H)+1H-NMR (CDCl3): 2.15 (3H, s), 3.75 (2H, m), 3.82 (2H, m), 4.60 (1H, s), 4.82 (2H, s), 4.93 (1H, d), 5.03 (1H, d), 7.03–7.43 (10H, m)

2) Synthesis of 2-(2-chloroethoxy)methyl-4-(3-chlorophenyl)-5-cyano-6-methyl-1,4-dihydropyridine-3-carboxylic acid:

The title compound was obtained from 0.84 g (1.8 mmol) of benzyl 2-(2-chloroethoxy)methyl-4-(3-chlorophenyl)-5-cyano-6-methyl-1,4-dihydropyridine-3-carboxylate in the same manner as that of Example 1–3).

Yield: (quantitative yield) MS (ESI, m/z) 365 (M–H)–1H-NMR (CDCl3): 2.16 (3H, s), 3.75 (2H, m), 3.86 (2H, m), 4.57 (1H, s), 4.80 (2H, s), 7.14–7.26 (4H, m), 7.55 (1H, s)

3) Synthesis of 2-(2-chloroethoxy)methyl-4-(3-chlorophenyl)-5-cyano-3-(3,3-diphenylpropylcarbamoyl)-6-methyl-1,4-dihydropyridine:

The title compound was obtained from 0.35 g (0.95 mmol) of 2-(2-chloroethoxy)methyl-4-(3-chlorophenyl)-5-cyano-6-methyl-1,4-dihydropyridine-3-carboxylic acid in the same manner as that of Example 7–2).

Yield: 0.43 g (0.77 mmol) (80.9%) MS (ESI, m/z) 560 (M+H)+1H-NMR (CDCl3): 2.07 (3H, s), 2.11 (2H, m), 3.08 (2H, q), 3.59 (1H, t), 3.71(2H, m), 3.80 (2H, m), 4.29 (1H, s), 4.84 (2H, s), 5.35 (1H, t), 7.05–7.35 (15H, m)

4) Synthesis of 2-(2-azidoethoxy)methyl-4-(3-chlorophenyl)-5-cyano-3-(3,3-diphenylpropylcarbamoyl)-6-methyl-1,4-dihydropyridine:

The title compound was obtained from 0.43 g (0.77 mmol) of 2-(2-chloroethoxy)methyl-4-(3-chlorophenyl)-5-cyano-3-(3,3-diphenylpropylcarbamoyl)-6-methyl-1,4-dihydropyridine in the same manner as that of Example 11–4).

MS (ESI, m/z) 567 (M+H)+1H-NMR (CDCl3): 2.07 (3H, s), 2.10 (2H, m), 3.07 (2H, m), 3.48 (2H, m), 3.58 (1H, t), 3.75 (2H, m), 4.25 (1H, s), 4.84 (2H, s), 5.26 (1H, t) 7.05–7.35 (15H, m)

5) Synthesis of 2-(2-aminoethoxy)methyl-4-(3-chlorophenyl)-5-cyano-3-(3,3-diphenylpropylcarbamoyl)-6-methyl-1,4-dihydropyridine:

The title compound was obtained from 0.40 g of 2-(2-azidoethoxy)methyl-4-(3-chlorophenyl)-5-cyano-3-(3,3-diphenylpropyl-carbamoyl)-6-methyl-1,4-dihydropyridine in the same manner as that of Example 1–3).

Yield: 151 mg (0.28 mmol) (36.3%) (2 steps) MS (ESI, m/z) 539 (M–H)–1H-NMR (CDCl3): 2.08 (3H, s), 2.10 (2H, m), 2.96 (2H, t), 3.08 (2H, m), 3.50–3.65 (3H, m), 4.24 (1H, s), 4.78 (1H, d), 4.84 (1H, d), 5.19 (1H, t), 7.05–7.38 (14H, m), 8.36 (1H, s)

The formulae of the compounds obtained in Examples 1 to 12 are shown in the following table, wherein the numerals correspond to the numbers of Examples.

| Example | Structure |
|---|---|
| 1 | 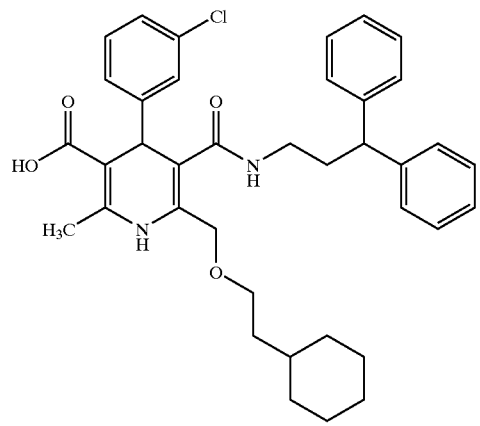 |
| 2 | 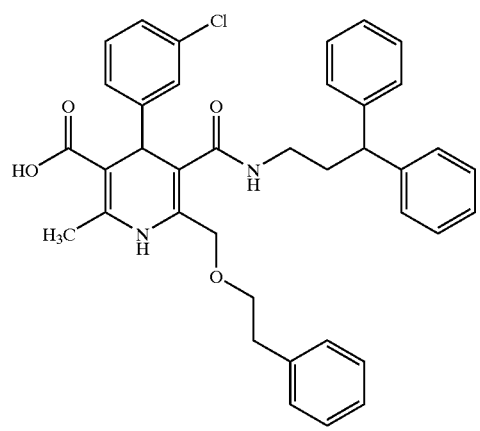 |
| 3 | 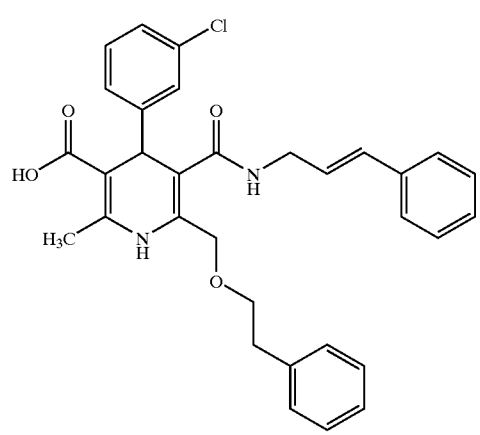 |
| 4 | 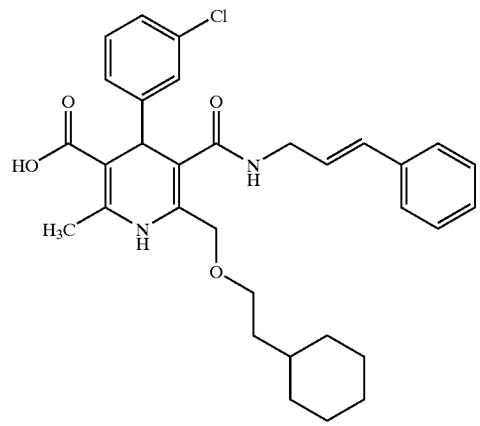 |

TEST EXAMPLE

Antagonistic Activity on L-type Calcium Channel

The activity of the dihydropyridine derivatives of the present invention to inhibit L-type calcium channel was determined by the following method in which the relaxation reaction on the KCl contraction of samples of thoracic aorta extracted from rats was employed.

1) Method of Preparation of Samples of Thoracic Aorta Extracted from Rats

The slips of thoracic aorta extracted from a Sprague-Dawry rat was used. The blood vessels were cut to obtain ring-shaped samples having a width of about 3 mm. The endothelial cells of the blood vessel were mechanically removed. The samples were suspended in a strain gage in Tyrode's solution (158.3 mM of NaCl, 4.0 mM of KCl, 1.05 mM of $MgCl_2$, 0.42 mM of $NaH_2PO_4$, 10 mM of $NaHCO_3$, 2 mM of $CaCl_2$ and 5 mM of glucose) in which a gaseous mixture of $O_2$ (95%) and $CO_2$ (5%) was introduced. A static tension of 2 g was applied hereto. The tension of the blood vessel was amplified with transducer and a tension amplifier (EF-601G; Nihon Koden Corporation) and recorded with a multi-pen recorder (Rikadenki Kogyo Co., Ltd.). The experiments were conducted at 37° C.

2) Determination of Relaxation After KCl Contraction

After the tension had been stabilized, the nutrient solution in the sample tank was replaced with High $K^+$ Tyrode's solution (112.3 mM of NaCl, 50 mM of KCl, 1.05 mM of $MgCl_2$, 0.42 mM of $NaH_2PO_4$, 10 mM of $NaHCO_3$, 2 mM of $CaCl_2$ and 5 mM of glucose) to conduct the contraction reaction. 30 minutes after, the solution in the sample tank was replaced with the normal Tyrode's solution. The solution in the sample tank was again replaced with the High $K^+$ Tyrode's solution and the contraction reaction was observed. After attaining the maximum contraction reaction, the test compound was cumulatively added at intervals of 90 minutes to attain concentrations of $10^{-7}$, $10^{-6}$ and $10^{-5}$M. The rate of the test compound to control the maximum contraction reaction was employed as the index of the inhibition activity on L-type calcium channel.

TEST EXAMPLE

Antagonistic Activity on N-type Calcium Channel
(Fluorescence Dye Method)

Human neuroblastoma cells IMR-32 were obtained from ATCC (American Type Culture Collection). The medium used was a Phenol Red-free Eagle minimum essential medium (GIBCO) containing earle's salts supplement, 2 mM of L-glutamine (GIBCO), 1 mM of sodium pyruvate (pH 6.5) (GIBCO), antibiotic/antimicotic mixture (GIBCO) and 10% fetal calf serum (Cell Culture Technologies). 3 ml of $1×10^5$/ml IMR-32 cells were spread on a glass dish (Iwaki Glass Co., Ltd.) having a diameter of 35 mm which was treated with poly-D-lysin (SIGMA) and collagen (COLLAGEN VITROGEN 100, Collagen Colo.). After the culture for 2 days, 1 mM (final concentration) of dibutyl cAMP and 2.5 $\mu$M of bromodeoxyuridine (SIGMA) were added. After the culture for additional 10 to 14 days, the cells were subjected to the activity determination. The medium for IMR-32 cells thus prepared was replaced with 1 ml of Phenol Red-free Eagle minimum essential medium (GIBCO) containing 1 ml of 10 $\mu$M fura-2/AM (Dojin Kagaku, Co.) and earle's salts supplement, and the incubation was conducted at 25° C. for 1 hour.

Then the medium was replaced with Phenol Red-free Eagle minimum essential medium (GIBCO) containing earle's salts supplement, from which fura-2/AM had been removed. After the incubation at 37° C. for 1 hour, the medium was replaced with a recording medium (20 mM of HEPES-KOH, 115 mM of NaCl, 5.4 mM of KCl, 0.8 mM of $MgCl_2$, 1.8 mM of $CaCl_2$ and 13.8 mM of D-glucose). Antagonistic activity on N-type calcium channel was determined and analyzed by using a fluorescence microscope (Nikon Corporation) and an image analysis device ARGUS 50 (Hamamatsu Photonics). In particular, a recording medium (20 mM of HEPES-KOH, 115 mM of NaCl, 5.4 mM of KCl, 0.8 mM of $MgCl_2$, 1.8 mM of $CaCl_2$ and 13.8 mM of D-glucose) containing 1 $\mu$M of Nifedipine was given to the cells by reflux by a Y-tube method. Then a stimulating agent containing 60 mM of potassium chloride was rapidly given by the Y-tube method. Thereafter stimulating agents containing 60 mM of potassium chloride and 0.1, 1 or 10 $\mu$M of test compound were successively rapidly given by the Y-tube method to determine the antagonistic activity on the channel. Finally, a stimulating agent containing 60 mM of potassium chloride and 1 $\mu$M of omega conotoxin GVIA (Peptide institute, inc.) was rapidly given by the Y-tube method to realize a condition of 100% inhibition of N-type calcium channel.

Table 2 shows the results of the determination of the activity of inhibiting the N-type calcium channel (pIC50) and L-type calcium channel (IC50). pIC50 indicates the antagonistic activity of the test compound. It is a negative logarithm of a concentration of a medicine necessitated for 50% inhibition.

TABLE 2

| Example | N-type inhibition pIC50 | L-type inhibition IC50 |
|---|---|---|
| 3 | 5.7 | 5.3 |
| 4 | 6.4 | 5.3 |

The same procedure as that of the above-described tests was repeated except for the following changes: 60 mM of potassium chloride-containing stimulating agent was rapidly given by the Y-tube method while the calcium concentration change in the cells was examined in terms of N-type calcium channel activity. Then Stimulating agents containing 60 mM of potassium chloride and 0.1, 1 or 10 $\mu$M of test compound were successively and rapidly given by the Y-tube method. A change in calcium concentration in the cells was determined. N-type calcium channel antagonistic activities calculated from the inhibition rates are shown in Table 3.

TABLE 3

| Example | N-type inhibition pIC50 | L-type inhibition IC50 |
|---|---|---|
| 3 | 5.6 | 5.3 |
| 4 | 6.1 | 5.8 |
| 6 | 5.6 | 5.6 |
| 11 | 5.7 | 5.9 |

Thus it is apparent that the new dihydropyridine derivatives have excellent N-type calcium channel antagonistic activity.

L-type calcium channel antagonistic activity of the compounds was also examined to find that the activity of them was only weak. They were thus highly selective to N-type calcium channel.

The new dihydropyridine derivatives of the present invention had selective N-type calcium channel antagonistic activity. Thus, the new dihydropyridine derivatives of the present invention are effective in the treatment of acute stage of ischemic cerebrovascular disorders caused by cerebral infarction or intracerebral bleeding (including subarachnoidal hemorrhage); progressive neurodegenerative diseases such as Alzheimer's disease, AIDS related dementia, Parkinson's disease, dementia due to cerebrovascular disorder and ALS; cerebral disorders caused by head injury; pains and cold flush caused by diabetes or thromboangiitis obliterans; various pains such as postoperative pain, migraine and visceral pain; various diseases associated with psychogenic stress such as bronchial asthma, unstable angina and irritable colitis; emotional disorder and withdrawal symptoms after addiction to drugs such as ethanol addiction withdrawal symptoms.

What is claimed is:

1. A dihydropyridine compound represented by the formula (1) or a pharmaceutically acceptable salt thereof:

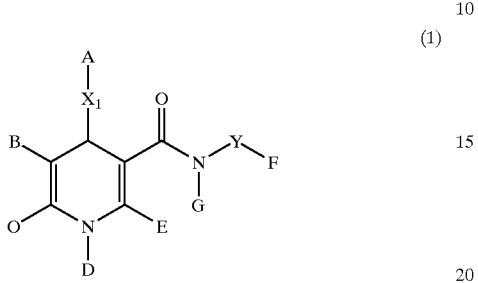

(1)

wherein

A represents a group of the formula (2), or 1-naphthyl, 2-naphthyl, thiophene-3-yl, thiophene-2-yl, furan-3-yl, furan-2-yl, pyridine-4-yl, pyridine-3-yl, pyridine-2-yl, indole-2-yl or indole-3-yl group:

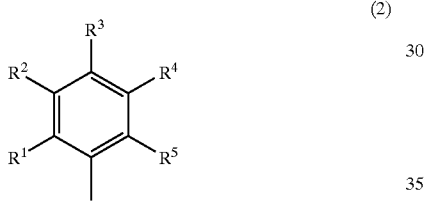

(2)

wherein $R^1$, $R^2$, $R^3$, $R^4$ and $R^5$ may be the same or different from each other and each represent hydrogen atom, a halogen atom, hydroxyl group, carboxyl group, amino group, cyano group, a nitro group, a lower alkyl group, a lower alkoxyl group, a lower alkenyl group, a lower alkynyl group, a lower alkylamino group, a lower alkylthio group, a lower alkanoyl group, a lower alkoxycarbonyl group, a hydroxy-lower alkyl group, a hydroxy-lower alkoxyl group, a hydroxy-lower alkenyl group, a halogeno-lower alkyl group, a halogeno-lower alkoxyl group, a halogeno-lower alkenyl group, an aryl group, a heteroaryl group, an aryl-lower alkoxyl group or an aroyl group, B represents cyano group, nitro group, acetyl group, tetrazole group, triazole group or a group of the formula (3) or (4):

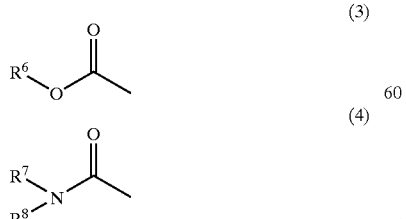

(3)

(4)

wherein $R^6$ to $R^8$ each represent hydrogen atom, a linear, branched or cyclic, saturated or unsaturated hydrocarbon group having 1 to 6 carbon atoms, an alkyl group substituted with a cyclic alkyl group which may contain a hetero atom, a substituted or unsubstituted aryl group, a substituted or unsubstituted heteroaryl group, a hydroxy-lower alkyl group, a hydroxy-lower alkenyl group, a halogeno-lower alkyl group, a halogeno-lower alkenyl group, an aryl-lower alkyl group, an aryl-lower alkenyl group, a heteroaryl-lower alkyl group (excluding pyridine-3-ylpropyl group), a heteroaryl-lower alkenyl group, a cyano-lower alkyl group or a cyano-lower alkenyl group, or $R^7$ and $R^8$ may together form a ring which may contain a hetero atom, C represents hydrogen atom, a lower alkyl group, dimethoxymethyl group, cyano group, a hydroxy-lower alkyl group, a halogeno-lower alkyl group (C does not represent these groups listed above when E represents hydrogen atom, a lower alkyl group, dimethoxymethyl group, cyano group, a hydroxy lower alkyl group or a halogeno-lower alkyl group), a substituted or unsubstituted amino-lower alkyl group (the substituent represents hydrogen atom or a lower alkyl group), an azido-lower alkyl group, an aryl group, a heteroaryl group, an aryl-lower alkyl group, a heteroaryl-lower alkyl group or a lower alkyl group substituted with a cyclic alkyl group which may contain a hetero atom in the group, D represents hydrogen atom, a lower alkyl group, a hydroxy-lower alkyl group or an aryl-lower alkyl group, E represents hydrogen atom, a lower alkyl group, dimethoxymethyl group, cyano group, a hydroxy-lower alkyl group, a halogeno-lower alkyl group (E does not represent these groups listed above when C represents hydrogen atom, a lower alkyl group, dimethoxymethyl group, cyano group, a hydroxy lower alkyl group or a halogeno-lower alkyl group), a substituted or unsubstituted amino-lower alkyl group (the substituent represents hydrogen atom or a lower alkyl group, and if necessary, they may contain a hetero atom in the chain thereof), an azido-lower alkyl group, an aryl group, a heteroaryl group, an aryl-lower alkyl group, a heteroaryl-lower alkyl group or a lower alkyl group substituted with a cyclic alkyl group which may contain a hetero atom in the group, F represents an aryl group, a heteroaryl group or a cyclic alkyl group which may contain a hetero atom in the group, excluding piperidinyl group and piperazinyl group, G represents hydrogen atom or a lower alkyl group, $X_1$ represents an interatomic bond, —CH$_2$—, —CH$_2$CH$_2$—, —CH=CH— or —C≡C—, and Y represents a group represented by any of the following formulae (5) to (14):

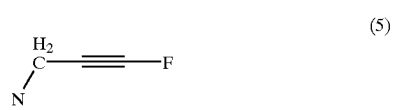

(5)

-continued

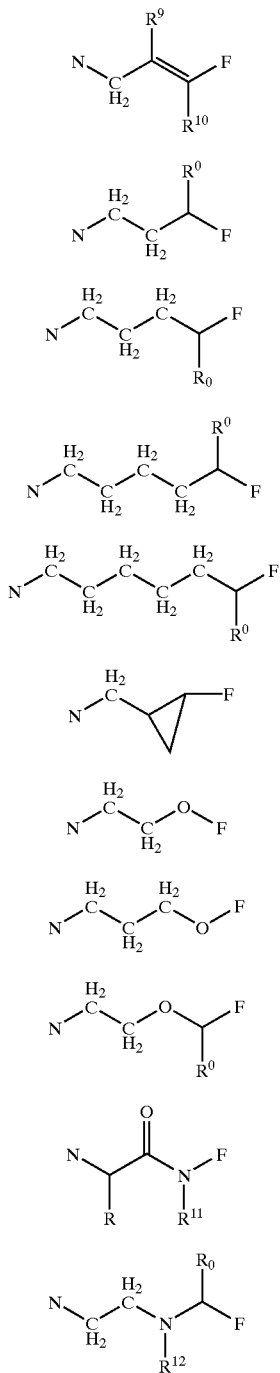

wherein
R⁹ to R¹², R and R⁰ may the same or different from each other, and they each represent hydrogen atom, a lower alkyl group, a hydroxy-lower alkyl group, a thio-lower alkyl group, an alkylthio-lower alkyl group, an aryl group, an aryl-lower alkyl group or a heteroaryl-lower alkyl group, B and C may together form a lactone ring or a lactam ring, two of $R^1$ to $R^3$ may be bonded together to form a ring, $R^9$ and $R^{10}$ be bonded together to form a ring, and $R^0$ may be condensed with F to form a ring.

2. The dihydropyridine compound or a pharmaceutically acceptable salt thereof of claim 1, wherein F represents a group of the formula (15), thiophene-3-yl group, thiophene-2-yl group, furan-3-yl group, furan-2-yl group, pyridine-4-yl group, pyridine-3-yl group, pyridine-2-yl group, cyclohexyl group, morpholine-4-yl group, imidazole-1-yl group or pyrrolidinone-1-yl group:

(15)

wherein $R^{13}$, $R^{14}$, $R^{15}$ $R^{16}$ and $R^{17}$ may be the same or different from each other and each represent hydrogen atom, a halogen atom, hydroxyl group, carboxyl group, amino group, cyano group, nitro group, a lower alkyl group, a lower alkoxyl group, a lower alkenyl group, a lower alkynyl group, a lower alkylamino group, a lower alkylthio group, a lower alkanoyl group, a hydroxy-lower alkyl group, a hydroxy-lower alkoxyl group, a hydroxy-lower alkenyl 10 group, a halogeno-lower alkyl group, a halogeno-lower alkoxyl group, a halogeno-lower alkenyl group, an aryl-lower alkyl group, an aryl-lower alkoxyl group, a lower alkoxycarbonyl group, carbamoyl group which may have a substituent, a carboxyamido group which may have a substituent, an aroyl group, an aryl group, a heteroaryl group or a saturated cyclic hydrocarbon group having 3 to 8 carbon atoms, and two of $R^{13}$ to $R^{16}$ may be bonded together to form a ring.

3. The dihydropyridine compound or a pharmaceutically acceptable salt thereof of claim 2, wherein Y represents a group of the formula (6).

4. The dihydropyridine compound or a pharmaceutically acceptable salt thereof according to claim 2, wherein Y represents a group of the formula (7), (8)-1, (8)-2 or (8)-3.

5. The dihydropyridine compound or a pharmaceutically acceptable salt thereof according to claim 2, wherein C represents a substituted or unsubstituted lower alkyl group, an amino-lower alkyl group wherein the substituent represents hydrogen atom or a lower alkyl group, an azido-lower alkyl group, an aryl group, a heteroaryl group, an aryl-lower alkyl group, a heteroaryl-lower alkyl groups or a lower alkyl group substituted with a cyclic alkyl group which may contain a hetero atom in the ring thereof.

6. The dihydropyridine compound or a pharmaceutically acceptable salt thereof according to claim 2, wherein E represents a substituted or unsubstituted amino-lower alkyl group wherein the substituent represents hydrogen atom or a lower alkyl group, an azido-lower alkyl group, an aryl group, a heteroaryl group, an aryl-lower alkyl group, a heteroaryl-lower alkyl group or a lower alkyl group substituted with a cyclic alkyl group which may contain a hetero atom in the ring thereof.

7. The dihydropyridine compound or a pharmaceutically acceptable salt thereof according to claim 2, wherein E represents a substituted or unsubstituted lower alkyl group.

8. The dihydropyridine compound or a pharmaceutically acceptable salt thereof according to claim 2, wherein D represents hydrogen atom, G represents hydrogen atom, $X_1$ represents an interatomic bond, and Y represents a group of the formula (6) wherein $R^9$ and $R^{10}$ each represent hydrogen atom.

9. The dihydropyridine compound or a pharmaceutically acceptable salt thereof according to claim 2, wherein D represents hydrogen atom, G represents hydrogen atom, $X_1$ represents an interatomic bond, and Y represents a group of the formula (7), (8)-1, (8)-2 or (8)-3.

10. The dihydropyridine compound or a pharmaceutically acceptable salt thereof according to claim 2, wherein B represents a group of the formula (3) or a group of the formula (4) wherein either $R^7$ $R^8$ represents hydrogen atom or B and C are condensed together to form a lactone ring, D represents hydrogen atom, G represents hydrogen atom, $X_1$ represents an interatomic bond and Y represents a group of the formula (6) wherein $R^9$ and $R^{10}$ each represent hydrogen atom, a group of the formula (7) or a group of the formula (8)-1, (8)-2 or (8)-3.

11. The dihydropyridine compound or a pharmaceutically acceptable salt thereof according to claim 2, wherein B represents a group of the formula (3), wherein $R^S$ represents hydrogen group, or a group of the formula (4) wherein either $R^7$ or $R^8$ represents hydrogen atom, D represents hydrogen atom, G represents hydrogen atom, $X_1$ represents an interatomic bond and Y represents a group of the formula (6) wherein $R^9$ and $R^{10}$ each represent hydrogen atom, a group of the formula (7) or a group of the formula (8)-1, (8)-2 or (8)-3 .

12. The dihydropyridine compound or a pharmaceutically acceptable salt thereof according to claim 2, wherein B represents a group of the formula (3), wherein $R^6$ represents hydrogen group, D represents hydrogen atom, G represents hydrogen atom, $X_1$ represents an interatomic bond and Y represents a group of the formula (6), wherein $R^9$ and $R^{10}$ each represent hydrogen atom, a group of the formula (7) or a group of the formula (8)-1, (8)-2 or (8)-3.

13. The dihydropyridine compound or a pharmaceutically acceptable salt thereof according to claim 2, wherein B represents a group of the formula (3), C represents any of substituted or unsubstituted lower alkyl groups and amino-lower alkyl groups, wherein the substituent represents a lower alkyl group, an azido-lower alkyl group, an aryl group, a heteroaryl group, an aryl lower alkyl group, a heteroaryl-lower alkyl group or a lower alkyl group substituted with a cyclic alkyl group which may contain a hetero atom, D represents hydrogen atom, G represents hydrogen atom and $X_1$ represents an interatomic bond.

14. The dihydropyridine compound or a pharmaceutically acceptable salt thereof according to claim 2, wherein B represents a group of the formula (3), D represents hydrogen atom, E represents any of substituted or unsubstituted amino-lower alkyl groups, wherein the substituent represents hydrogen atom or a lower alkyl group, an azido-lower alkyl group, an aryl group, a heteroaryl group, an aryl-lower alkyl group, a heteroaryl-lower alkyl group, a lower alkyl group substituted with a cyclic alkyl group which may contain a hetero atom, G represents hydrogen atom, and $X_1$ represents an interatomic bond.

15. The dihydropyridine compound or a pharmaceutically acceptable salt thereof according to claim 2, wherein B represents a group of the formula (3), D represents hydrogen atom, E represents a substituted or unsubstituted lower alkyl group, G represents hydrogen atom, and $X_1$ represents an interatomic bond.

16. The dihydropyridine compound or a pharmaceutically acceptable salt thereof according to claim 2, wherein B represents a group of the formula (3) wherein $R^6$ represents hydrogen atom, C represents a lower alkyl group, an aryl-lower alkyl group, a heteroaryl-lower alkyl group or a lower alkyl group substituted with a cyclic alkyl group which may contain a hetero atom, D represents hydrogen atom, G represents hydrogen atom, and $X_1$ represents an interatomic bond.

17. The dihydropyridine compound or a pharmaceutically acceptable salt thereof according to claim 2, wherein B represents a group of the formula (3), wherein $R^6$ represents hydrogen atom, D represents hydrogen atom, E represents an aryl-lower alkyl group, a heteroaryl-lower alkyl group or a lower alkyl group substituted with a cyclic alkyl group which may contain a hetero atom, G represents hydrogen atom, and $X_1$ represents an interatomic bond.

18. The dihydropyridine compound or a pharmaceutically acceptable salt thereof according to claim 2, wherein B represents a group of the formula (3), wherein $R^6$ represents a hydrogen atom, D represents a hydrogen atom, E represents a lower alkyl group, G represents a hydrogen atom, and $X_1$ represents an interatomic bond.

19. The dihydropyridine compound or a pharmaceutically acceptable salt thereof according to claim 2, wherein A represents a group of the formula (2), B represents a group of formula (3), wherein $R^6$ represents a hydrogen group, D represents a hydrogen atom, F represents a group of the formula (15), G represents a hydrogen atom, $X_1$ represents an interatomic bond and Y represents a group of the formula (6) wherein $R^9$ and $R^{10}$ each represent hydrogen atom, a group of the formula (7) or a group of the formula (8)-1, (8)-2 or (8)-3 .

20. The dihydropyridine compound or a pharmaceutically acceptable salt thereof according to claim 1, wherein $R^1$, $R^2$, $R^3$, $R^4$ and $R^5$ may be the same or different from each other and each represent hydrogen atom, a halogen atom, hydroxyl group, carboxyl group, amino group, cyano group, a lower alkyl group, a lower alkoxyl group, a lower alkenyl group, a lower alkynyl group, a lower alkylamino group, a lower alkylthio group, a lower alkanoyl group, a lower alkoxycarbonyl group, a hydroxy-lower alkyl group, a hydroxy-lower alkoxyl group, a hydroxy-lower alkenyl group, a halogeno-lower alkyl group, a halogeno-lower alkoxyl group, a halogeno-lower alkenyl group, an aryl group, a heteroaryl group, an aryl-lower alkoxyl group or an aroyl group.

21. The dihydropyridine compound or a pharmaceutically acceptable salt thereof according to claim 1, wherein A represents a group of the formula (2):

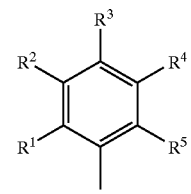

(2)

wherein $R^1$, $R^2$, $R^3$, $R^4$ and $R^5$ may be the same or different from each other and each represent hydrogen atom, a halogen atom, hydroxyl group, carboxyl group, amino group, cyano group, a lower alkyl group, a lower alkoxyl group, a lower alkenyl group, a lower alkynyl group, a lower alkylamino group, a lower alkylthio group, a lower alkanoyl group, a lower alkoxycarbonyl group, a hydroxy-lower alkyl group, a hydroxy-lower alkoxyl group, a hydroxy-lower alkenyl group, a halogeno-lower alkyl group, a halogeno-lower alkoxyl group, a halogeno-lower alkenyl group, an aryl group, a heteroaryl group, an aryl-lower alkoxyl group or an aroyl group.

22. A pharmaceutical composition comprising the dihydropyridine compound or a pharmaceutically acceptable salt thereof according to claim 1.

23. A method of treating acute stage of ischemic cerebrovascular disorders caused by cerebral infarction or intracerebral bleeding, comprising administering an effective amount of the dihydropyridine compound or a pharmaceutically acceptable salt thereof of claim 1 to a subject in need thereof.

24. A method of treating neuropathy caused by head injury, comprising administering an effective amount of the dihydropyridine compound or a pharmaceutically acceptable salt thereof of claim 1 to a subject in need thereof.

25. A method of treating pain caused by thromboangiitis obliterans, comprising administering an effective amount of a dihydropyridine compound or the pharmaceutically acceptable salt thereof of claim 1 to a subject in need thereof.

26. A method of treating postoperative pain, comprising administering an effective amount of the dihydropyridine compound or a pharmaceutically acceptable salt thereof of claim 1 to a subject in need thereof.

27. A method of treating migraine, comprising administering an effective amount of the dihydropyridine compound or a pharmaceutically acceptable salt thereof of claim 1 to a subject in need thereof.

28. A method of treating visceral pain, comprising administering an effective amount of the dihydropyridine compound or a pharmaceutically acceptable salt thereof of claim 1 to a subject in need thereof.

* * * * *